United States Patent
Benting et al.

(10) Patent No.: US 8,349,884 B2
(45) Date of Patent: Jan. 8, 2013

(54) FUNGICIDE N-CYCLOALKYL-N-BICYCLIMETHYLENE-CARBOXAMIDE DERIVATIVES

(75) Inventors: Jurgen Benting, Leichlingen (DE); Peter Dahmen, Neuss (DE); Philippe Desbordes, Lyons (FR); Stephanie Gary, Champagne au Mont d'Or (FR); Pierre Genix, Lyons (FR); Benoit Hartmann, Sainte Foy-les-Lyons (FR)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 13/146,633

(22) PCT Filed: Jan. 27, 2010

(86) PCT No.: PCT/EP2010/050883
§ 371 (c)(1),
(2), (4) Date: Jul. 27, 2011

(87) PCT Pub. No.: WO2010/086311
PCT Pub. Date: Aug. 5, 2010

(65) Prior Publication Data
US 2011/0294863 A1    Dec. 1, 2011

(30) Foreign Application Priority Data

Jan. 28, 2009   (EP) ..................... 09356003

(51) Int. Cl.
A61K 31/415   (2006.01)
C07D 231/10   (2006.01)
(52) U.S. Cl. ..................................... 514/406
(58) Field of Classification Search .............. 514/406; 548/374.1
See application file for complete search history.

(56) References Cited

FOREIGN PATENT DOCUMENTS

| EP | 1772449 | 4/2007 |
|---|---|---|
| EP | 1792901 | 6/2007 |
| WO | WO 2007/087906 | 8/2007 |

OTHER PUBLICATIONS

International Search Report issued Mar. 4, 2010 in corresponding International Application No. PCT/EP2010/050883.
M.P. De Ninno et al.: "Synthesis and Dopaminergic Activity of 3-Substituted 1-(Aminomethy)-3,4-dihydro-5,6-dihydroxy-1H-2-benzopyrans: Characterization of an Auxiliary Binding Region in the D1 Receptor", *J. Med. Chem.*, vol. 34, No. 8, 1991, pp. 2561-2569, XP002528845.
M.D. Meyer, et al.: Structure-Activity Studies for a Novel Series of N-(Arylethyl)-N-(1,2,3,4-tetrahydronaphthalen-1-ylmeth1)-N-methylamines Possessing Dual 5-HT Uptake Inhibiting and $\alpha_2$-Antagonistic Activities, 1997.

*Primary Examiner* — Rebecca Anderson
*Assistant Examiner* — Samantha Shterengarts
(74) *Attorney, Agent, or Firm* — Ostrolenk Faber LLP

(57) ABSTRACT

The present invention relates N-cycloalkyl-N-bicyclicmethylene-carboxamide, thiocarboxamide or N-substituted carboximidamide derivatives of formula (I) wherein A represents a carbo-linked, 5-membered heterocyclyl group, T represents O or S, $Z^1$ represents a $C_3$-$C_7$-cycloalkyl group, X represents N or a $CZ^7$ and $Y^1$, $Y^2$, $Z^2$, $Z^3$, $L^1$ and $L^2$ represent various substituents, their process of preparation, the preparation of intermediate compounds, their use as fungicide active agents, particularly in the form of fungicide compositions and methods for the control of phytopathogenic fungi, notably of plants, using these compounds or compositions.

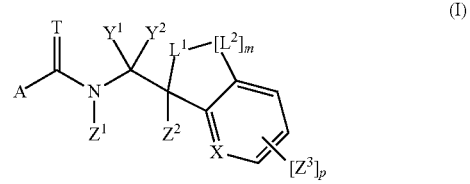

18 Claims, No Drawings

FUNGICIDE N-CYCLOALKYL-N-BICYCLIMETHYLENE-CARBOXAMIDE DERIVATIVES

CROSS-REFERENCE TO RELATED APPLICATION(S)

The present application is a 35 U.S.C. §371 national phase conversion of PCT/EP2010/050883 filed Jan. 27, 2010, which claims priority of European Application No. 09356003.5 filed Jan. 28, 2009. Applicants claim priority to each of the foregoing patent applications. The PCT International Application was published in the English language.

The present invention relates to N-cycloalkyl-N-bicyclic-methylene-carboxamide or thiocarboxamide derivatives, their process of preparation, preparation of intermediate compounds, their use as fungicide active agents, particularly in the form of fungicide compositions, and methods for the control of phytopathogenic fungi, notably of plants, using these compounds or compositions.

In international patent application WO2007060164 certain phenethyl amides are generically embraced in a broad disclosure of numerous compounds of the following formula:

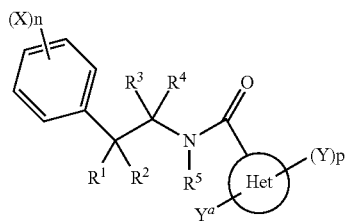

wherein Het represent a 5-, 6- or 7-membered heterocycle with 1 to 3 heteroatoms. Het being linked by a carbon atom. However, this document does not specifically disclose nor suggest compounds wherein R1 or R2 together with X (in the ortho-position) form a ring fused to the phenyl ring.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds that possess the above mentioned effects or advantages.

Accordingly, the present invention provides N-cycloalkyl-N-bicyclicmethylene-carboxamide or thiocarboxamide derivatives of formula (I)

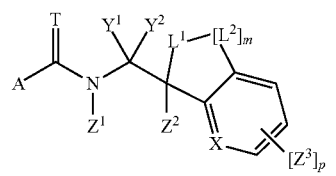

wherein
A represents a carbo-linked, partially saturated or unsaturated, 5-membered heterocyclyl group that can be substituted by up to four groups R that can be the same or different, T represents O or S,
$Z^1$ represents a non substituted $C_3$-$C_7$-cycloalkyl or a $C_3$-$C_7$ cycloalkyl substituted by up to 10 atoms or groups that can be the same or different and that can be selected in the list consisting of halogen atoms, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, di-$C_1$-$C_8$-alkylaminocarbonyl or carbamoyl,
$Z^2$ represents a hydrogen atom, a halogen atom, hydroxyl group, cyano, $C_1$-$C_8$-alkyl, $C_1$-$C_8$-alkoxy, $C_1$-$C_8$-halogenoalkyl comprising up to 9 halogen atoms that can be the same or different, amino or $C_1$-$C_8$-alkylamino,
$Y^1$ and $Y^2$ independently represents a hydrogen atom, a halogen atom, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, di-$C_1$-$C_8$-alkylaminocarbonyl or carbamoyl,
$L^1$ and $L^2$ independently represents $CZ^4Z^5$, $NZ^6$, O, S, S(O) or $S(O)_2$,
m represents 1, 2 or 3,
X represents $CZ^7$ or N,
$Z^3$ and $Z^7$ independently represents a hydrogen atom, a halogen atom, nitro, cyano, hydroxyl, thio, amino, pentafluoro-λ6-thio, $C_1$-$C_8$-alkyl, $C_1$-$C_8$-halogenoalkyl comprising up to 9 halogen atoms that can be the same or different, $C_1$-$C_8$-arylalkyl, $C_1$-$C_8$-alkylamino, di-$C_1$-$C_8$-alkylamino, $C_1$-$C_8$-alkoxy, $C_1$-$C_8$-halogenoalkoxy comprising up to 9 halogen atoms that can be the same or different, $C_1$-$C_8$-alkoxy-$C_1$-$C_8$-alkyl, $C_1$-$C_8$-alkylsulphanyl, $C_1$-$C_8$-halogenoalkylsulphanyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-arylalkenyl, ($C_3$-$C_7$-cycloalkyl)-$C_1$-$C_8$-alkenyl, $C_2$-$C_8$-alkynyl, $C_2$-$C_8$-halogenoalkynyl comprising up to 9 halogen atoms that can be the same or different, $C_2$-$C_8$-arylalkynyl, ($C_3$-$C_7$-cycloalkyl)-$C_1$-$C_8$-alkynyl, $C_2$-$C_8$-alkenyloxy, $C_2$-$C_8$-halogenoalkenyloxy comprising up to 9 halogen atoms that can be the same or different, $C_2$-$C_8$-alkynyloxy, $C_2$-$C_8$-halogenoalkynyloxy comprising up to 9 halogen atoms that can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms that can be the same or different, formyl, formyloxy, formylamino, carboxy, carbamoyl, N-hydroxycarbamoyl, carbamate, (hydroxyimino)-$C_1$-$C_8$-alkyl, $C_1$-$C_8$-alkylcarbonyl, $C_1$-$C_8$-halogenoalkylcarbonyl comprising up to 9 halogen atoms that can be the same or different, $C_1$-$C_8$-alkylcarbamoyl, di-$C_1$-$C_8$-alkylcarbamoyl, N—$C_1$-$C_8$-alkyloxycarbamoyl, $C_1$-$C_8$-alkoxycarbamoyl, N—$C_1$-$C_8$-alkyl-$C_1$-$C_8$-alkoxycarbamoyl, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, di-$C_1$-$C_8$-alkylaminocarbonyl, $C_1$-$C_8$-alkylcarbonyloxy, $C_1$-$C_8$-halogenoalkylcarbonyloxy comprising up to 9 halogen atoms that can be the same or different, $C_1$-$C_8$-alkylcarbonylamino, $C_1$-$C_8$-halogenoalkylcarbonylamino comprising up to 9 halogen atoms that can be the same or different, $C_1$-$C_8$-alkylaminocarbonyloxy, di-$C_1$-$C_8$-alkylaminocarbonyloxy, $C_1$-$C_8$-alkyloxycarbonyloxy, $C_1$-$C_8$-alkylsulphenyl, $C_1$-$C_8$-halogenoalkylsulphenyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, $C_1$-$C_8$-halogenoalkylsulphonyl comprising up to 9 halogen atoms that can be the same or different, $C_1$-$C_8$-alkoxyimino, ($C_1$-$C_8$-alkoxyimino)-$C_1$-$C_8$-alkyl, ($C_1$-$C_8$-alkenyloxyimino)-$C_1$-$C_8$-alkyl, ($C_1$-$C_8$-alkynyloxyimino)-$C_1$-$C_8$-alkyl, a (benzyloxyimino)-$C_1$-$C_8$-alkyl, tri($C_1$-$C_8$-alkyl)silyl, tri($C_1$-$C_8$-alkyl)silyl-$C_1$-$C_8$-alkyl, phenyl that can be substituted by up to 5 groups Q that can be the same or different, benzyloxy that can be substituted by up to 5 groups Q that can be the same or different, benzylthio that can be substituted by up to 5 groups Q that can be the same or different, benzylamino that can be substituted by up to 5 groups Q that can be the same or different, naphtyl that can be substituted by up to 6 groups Q that can be the same or different, phenoxy that can be substituted by up to 5 groups Q that can be the same or different, phenylamino that can be substituted by up to 5 groups Q that can be the same or different, phenylthio that can be substituted by up to 5 groups Q that can be the same or different, phenylmethylene that can be substituted by up to 5 groups Q that can be the same or different, pyridinyl that can be substituted by up to four groups Q that can be the same or different, pyridinyloxy that can be substituted by up to four groups Q that can be the same or different, or phenoxymethylene that can be substituted by up to 5 groups Q; or $Z^3$ or $Z^7$ together with the consecutive carbon atoms to which they are linked can form a 5- or 6-membered, saturated or non-saturated, carbo- or hetero-cycle, that can be substituted by up to four groups Q that can be the same or different, p represents 1, 2, or 3, R represents a hydrogen atom, halogen atom, cyano, nitro, amino, thio, pentafluoro-λ-6-thio, $C_1$-$C_8$-alkylamino, di-$C_1$-$C_8$-alkylamino, tri($C_1$-$C_8$-alkyl)silyl, $C_1$-$C_8$-alkylsulphanyl, $C_1$-$C_8$-halogenoalkylsulphanyl comprising up to 9 halogen atoms that can be the same or different, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_1$-$C_8$-alkoxy, $C_1$-$C_8$-halogenoalkoxy comprising up to 9 halogen atoms that can be the same or different, $C_2$-$C_8$-alkenyloxy, $C_2$-$C_8$-alkynyloxy, $C_3$-$C_7$-cycloalkyl, $C_3$-$C_7$-cycloalkyl-$C_1$-$C_8$-alkyl, $C_1$-$C_8$-alkylsulphinyl, $C_1$-$C_8$-alkylsulphonyl, $C_1$-$C_8$alkoxyimino, ($C_1$-$C_8$-alkoxyimino)-$C_1$-$C_8$-alkyl, (benzyloxyimino)-$C_1$-$C_8$-alkyl, phenoxy, benzyloxy, benzylthio, benzylamino, naphtyl, halogenophenoxy comprising up to 9 halogen atoms that can be the same or different, $C_1$-$C_8$-alkylcarbonyl, $C_1$-$C_8$-halogenoalkylcarbonyl comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, or di-$C_1$-$C_8$-alkylaminocarbonyl;

$Z^4$ and $Z^5$ independently represents a hydrogen atom, a halogen atoms, cyano, nitro, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxy-$C_1$-$C_8$-alkyl, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms that can be the same or different, formyl, $C_1$-$C_8$-alkylcarbonyl, $C_1$-$C_8$-halogenoalkylcarbonyl comprising up to 9 halogen atoms that can be the same or different, $C_1$-$C_8$-alkylsulphanyl, $C_1$-$C_8$-halogenoalkylsulphanyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, or $C_1$-$C_8$-halogenoalkylsulphonyl comprising up to 9 halogen atoms that can be the same or different, $Z^6$ represents a hydrogen atom, $C_1$-$C_8$-alkyl, $C_1$-$C_8$-halogenoalkyl comprising up to 9 halogen atoms that can be the same or different, $C_1$-$C_8$-alkoxy-$C_1$-$C_8$-alkyl, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms that can be the same or different, formyl, $C_1$-$C_8$-alkylcarbonyl, $C_1$-$C_8$-halogenoalkylcarbonyl comprising up to 9 halogen atoms that can be the same or different, $C_1$-$C_8$-alkylsulphonyl, $C_1$-$C_8$-halogenoalkylsulphonyl comprising up to 9 halogen atoms that can be the same or different, phenylsulfonyl can be substituted by up to 5 groups Q that can be the same or different, or benzyl that can be substituted by up to 5 groups Q that can be the same or different, Q represents a halogen atom, cyano, nitro, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkylsulphanyl, $C_1$-$C_8$-halogenoalkylsulphanyl comprising up to 9 halogen atoms that can be the same or different, tri($C_1$-$C_8$)alkylsilyl or tri($C_1$-$C_8$)alkylsilyl-$C_1$-$C_8$-alkyl, as well as salts, N-oxides, metallic complexes, metalloidic complexes and optically active or geometric isomers thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods that are known per se by the man ordinary skilled in the art.

According to the invention, the following generic terms are generally used with the following meanings:
  halogen means fluorine, chlorine, bromine or iodine,
  heteroatom can be nitrogen, oxygen or sulphur,
  halogenated groups, notably haloalkyl, haloalkoxy and cycloalkyl groups, can comprise up to nine identical or different halogen atoms, Any alkyl, alkenyl or alkynyl group can be linear or branched, the term "aryl" means phenyl or naphthyl, optionally substituted by one to five groups selected in the list consisting of halogen, $[C_1\text{-}C_6]$-alkyl, $[C_1\text{-}C_6]$-haloalkyl, $[C_2\text{-}C_6]$-alkenyl, $[C_2\text{-}C_6]$-haloalkenyl, $[C_2\text{-}C_6]$-alkynyl, $[C_2\text{-}C_6]$-haloalkynyl, $[C_1\text{-}C_6]$-alkoxy, $[C_1\text{-}C_4]$-alkoxy-$[C_1\text{-}C_4]$-alkyl, $[C_1\text{-}C_4]$-alkoxy-$[C_1\text{-}C_4]$-alkoxy, $[C_1\text{-}C_6]$-haloalkoxy and $[C_1\text{-}C_4]$-haloalkoxy-$[C_1\text{-}C_4]$-alkyl, In the case of an amino group or the amino moiety of any other amino-containing group, substituted by two substituents that can be the same or different, the two substituents together with the nitrogen atom to that they are linked can form a heterocyclyl group, preferably a 5- to 7-membered heterocyclyl group, that can be substituted or that can include other hetero atoms, for example a morpholino group or piperidinyl.

unless indicated otherwise, a group or a substituent that is substituted according to the invention can be substituted by one or more of the following groups or atoms: a halogen atom, a nitro group, a hydroxy group, a cyano group, an amino group, a sulphenyl group, a pentafluoro-$\lambda^6$-sulphenyl group, a formyl group, a substituted or non-substituted carbaldehyde O—($C_1\text{-}C_8$-alkyl)oxime, a formyloxy group, a formylamino group, a carbamoyl group, a N-hydroxycarbamoyl group, a formylamino group, a (hydroxyimino)-$C_1\text{-}C_6$-alkyl group, a $C_1\text{-}C_8$-alkyl, a tri($C_1\text{-}C_8$-alkyl)silyl-$C_1\text{-}C_8$-alkyl, $C_1\text{-}C_8$-cycloalkyl, tri($C_1\text{-}C_8$-alkyl)silyl-$C_1\text{-}C_8$-cycloalkyl, a $C_1\text{-}C_8$-halogenoalkyl having 1 to 5 halogen atoms, a $C_1\text{-}C_8$-halogenocycloalkyl having 1 to 5 halogen atoms, a $C_2\text{-}C_8$-alkenyl, a $C_2\text{-}C_8$-alkynyl, a $C_2\text{-}C_8$-alkenyloxy, a $C_2\text{-}C_8$-alkynyloxy, a $C_1\text{-}C_8$-alkylamino, a di-$C_1\text{-}C_8$-alkylamino, a $C_1\text{-}C_8$-alkoxy, a $C_1\text{-}C_8$-halogenoalkoxy having 1 to 5 halogen atoms, a $C_1\text{-}C_8$-alkylsulphenyl, a $C_1\text{-}C_8$-halogenoalkylsulphenyl having 1 to 5 halogen atoms, a $C_2\text{-}C_8$-alkenyloxy, a $C_2\text{-}C_8$-halogenoalkenyloxy having 1 to 5 halogen atoms, a $C_3\text{-}C_8$-alkynyloxy, a $C_3\text{-}C_8$-halogenoalkynyloxy having 1 to 5 halogen atoms, a $C_1\text{-}C_8$-alkylcarbonyl, a $C_1\text{-}C_8$-halogenoalkylcarbonyl having 1 to 5 halogen atoms, a $C_1\text{-}C_8$-alkylcarbamoyl, a di-$C_1\text{-}C_8$-alkylcarbamoyl, a N—$C_1\text{-}C_8$-alkyloxycarbamoyl, a $C_1\text{-}C_8$-alkoxycarbamoyl, a N—$C_1\text{-}C_8$-alkyl-$C_1\text{-}C_8$-alkoxycarbamoyl, a $C_1\text{-}C_8$-alkoxycarbonyl, a $C_1\text{-}C_8$-halogenoalkoxycarbonyl having 1 to 5 halogen atoms, a $C_1\text{-}C_8$-alkylcarbonyloxy, a $C_1\text{-}C_8$-halogenoalkylcarbonyloxy having 1 to 5 halogen atoms, a $C_1\text{-}C_8$-alkylcarbonylamino, a $C_1\text{-}C_8$-halogenoalkylcarbonylamino having 1 to 5 halogen atoms, substituted or non-substituted $C_1\text{-}C_8$-alkoxycarbonylamino, substituted or non-substituted $C_1\text{-}C_8$-halogenoalkoxycarbonylamino having 1 to 5 halogen atoms, a $C_1\text{-}C_8$-alkylaminocarbonyloxy, a di-$C_1\text{-}C_8$-alkylaminocarbonyloxy, a $C_1\text{-}C_8$-alkyloxycarbonyloxy, a $C_1\text{-}C_8$-alkylsulphenyl, a $C_1\text{-}C_8$-halogenoalkylsulphenyl having 1 to 5 halogen atoms, a $C_1\text{-}C_8$-alkylsulphinyl, a $C_1\text{-}C_8$-halogenoalkylsulphinyl having 1 to 5 halogen atoms, a $C_1\text{-}C_8$-alkylsulphonyl, a $C_1\text{-}C_8$-halogeno-alkylsulphonyl having 1 to 5 halogen atoms, a $C_1\text{-}C_8$-alkylaminosulfamoyl, a di-$C_1\text{-}C_8$-alkylaminosulfamoyl, a ($C_1\text{-}C_6$-alkoxyimino)-$C_1\text{-}C_6$-alkyl, a ($C_1\text{-}C_6$-alkenyloxyimino)-$C_1\text{-}C_6$-alkyl, a ($C_1\text{-}C_6$-alkynyloxyimino)-$C_1\text{-}C_6$-alkyl, a (benzyloxyimino)-$C_1\text{-}C_6$-alkyl, $C_1\text{-}C_8$-alkoxyalkyl, $C_1\text{-}C_8$-halogenoalkoxyalkyl having 1 to 5 halogen atoms, benzyloxy, benzylsulphenyl, benzylamino, phenoxy, phenylsulphenyl, or phenylamino;

Preferred compounds of formula (I) according to the invention are those wherein A is selected in the list consisting of:

a heterocycle of formula ($A^1$)

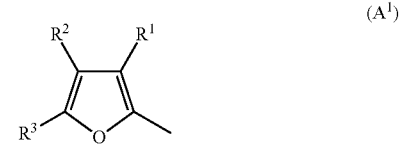

wherein:

$R^1$ to $R^3$ independently represents a hydrogen atom, a halogen atom, $C_1\text{-}C_5$-alkyl, $C_1\text{-}C_5$-halogenoalkyl comprising up to 9 halogen atoms that can be the same or different, $C_1\text{-}C_5$-alkoxy or $C_1\text{-}C_5$-halogenoalkoxy comprising up to 9 halogen atoms that can be the same or different, a heterocycle of formula ($A^2$)

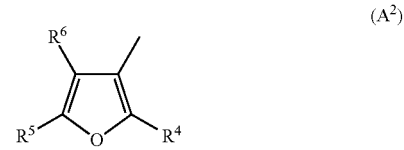

wherein:

$R^4$ to $R^6$ independently represents a hydrogen atom, a halogen atom, $C_1\text{-}C_5$-alkyl, $C_1\text{-}C_5$-halogenoalkyl comprising up to 9 halogen atoms that can be the same or different, $C_1\text{-}C_5$-alkoxy or $C_1\text{-}C_5$-halogenoalkoxy comprising up to 9 halogen atoms that can be the same or different, a heterocycle of formula ($A^3$)

wherein:

$R^7$ represents a hydrogen atom, a halogen atom, $C_1\text{-}C_5$-alkyl, $C_1\text{-}C_5$-halogenoalkyl comprising up to 9 halogen atoms that can be the same or different, $C_1\text{-}C_5$-alkoxy or $C_1\text{-}C_5$-halogenoalkoxy comprising up to 9 halogen atoms that can be the same or different;

$R^8$ represents a hydrogen atom or a $C_1\text{-}C_5$-alkyl, a heterocycle of formula ($A^4$)

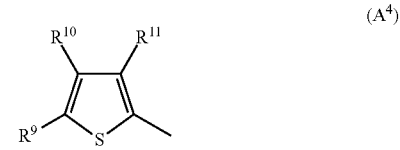

wherein:
$R^9$, $R^{10}$, $R^{11}$ independently represents a hydrogen atom, a halogen atom, $C_1$-$C_5$-alkyl, amino, $C_1$-$C_5$-alkoxy, $C_1$-$C_5$-alkylsulphanyl, $C_1$-$C_5$-halogenoalkyl comprising up to 9 halogen atoms that can be the same or different or $C_1$-$C_5$-halogenoalkoxy comprising up to 9 halogen atoms that can be the same or different, a heterocycle of formula ($A^5$)

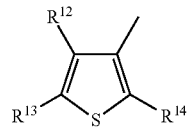

($A^5$)

wherein:
$R^{12}$, $R^{13}$, $R^{14}$ independently represents a hydrogen atom, a halogen atom, $C_1$-$C_5$-alkyl, $C_1$-$C_5$-alkoxy, amino, $C_1$-$C_5$-halogenoalkyl comprising up to 9 halogen atoms that can be the same or different or $C_1$-$C_5$-halogenoalkoxy comprising up to 9 halogen atoms that can be the same or different a heterocycle of formula ($A^6$)

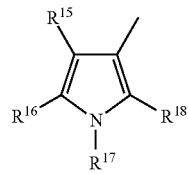

($A^6$)

wherein:
$R^{15}$ represents a hydrogen atom, a halogen atom, a cyano, $C_1$-$C_5$-alkyl, $C_1$-$C_5$-alkoxy, $C_1$-$C_5$-halogenoalkoxy comprising up to 9 halogen atoms that can be the same or different or $C_1$-$C_5$-halogenoalkyl comprising up to 9 halogen atoms that can be the same or different, $R^{16}$ and $R^{18}$ independently represents a hydrogen atom, a halogen atom, $C_1$-$C_5$-alkoxycarbonyl, $C_1$-$C_5$-alkyl, $C_1$-$C_5$-halogenoalkoxy comprising up to 9 halogen atoms that can be the same or different or $C_1$-$C_5$-halogenoalkyl comprising up to 9 halogen atoms that can be the same or different, $R^{17}$ represents a hydrogen atom or $C_1$-$C_5$-alkyl, a heterocycle of formula ($A^7$)

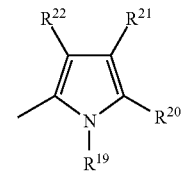

($A^7$)

wherein:
$R^{19}$ represents a hydrogen atom or a $C_1$-$C_5$-alkyl,
$R^{20}$, $R^{21}$, $R^{22}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, a heterocycle of formula ($A^8$)

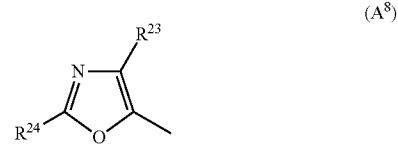

($A^8$)

wherein:
$R^{23}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, $R^{24}$ represents a hydrogen atom or $C_1$-$C_5$-alkyl or $C_1$-$C_5$-halogenoalkyl comprising up to 9 halogen atoms that can be the same or different, a heterocycle of formula ($A^9$)

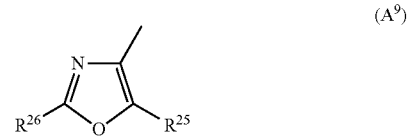

($A^9$)

wherein:
$R^{25}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, $R^{26}$ represents a hydrogen atom, $C_1$-$C_5$-alkyl or $C_1$-$C_5$-halogenoalkyl comprising up to 9 halogen atoms that can be the same or different, a heterocycle of formula ($A^{10}$)

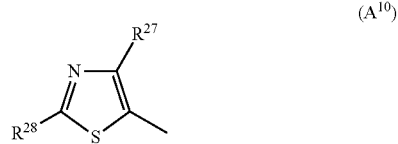

($A^{10}$)

wherein:
$R^{27}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, $R^{28}$ represents a hydrogen atom, a halogen atom, amino, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms which can be the same or different, $C_1$-$C_5$-alkylsulfanyl or $C_1$-$C_5$-halogenoalkylsulfanyl comprising up to 9 halogen atoms that can be the same or different, $C_1$-$C_5$-alkylamino or di($C_1$-$C_5$-alkyl)amino, a heterocycle of formula ($A^{11}$)

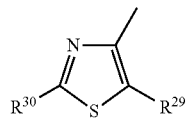

($A^{11}$)

wherein:
$R^{29}$ represents a hydrogen atom, a halogen atom, $C_1$-$C_5$-alkyl, $C_1$-$C_5$-alkoxy, $C_1$-$C_5$-halogenoalkoxy comprising up to 9 halogen atoms that can be the same or different or $C_1$-$C_5$-halogenoalkyl comprising up to 9 halogen atoms that can be the same or different, $R^{30}$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, $C_1$-$C_5$-alkylsulfanyl or $C_1$-$C_5$-halogenoalkylsulfanyl comprising up to 9 halogen atoms that can be the same or different, amino, $C_1$-$C_5$-alkylamino or di-$C_1$-$C_5$-alkylamino, a heterocycle of formula ($A^{12}$)

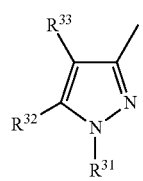

($A^{12}$)

wherein:
$R^{31}$ represents a hydrogen atom, a halogen atom or a $C_1$-$C_5$-alkyl,
$R^{32}$ represents a hydrogen atom, a halogen atom, $C_1$-$C_5$-alkyl or $C_1$-$C_5$-halogenoalkyl comprising up to 9 halogen atoms that can be the same or different,
$R^{33}$ represents a hydrogen atom, a halogen atom, a nitro, $C_1$-$C_5$-alkyl, $C_1$-$C_5$-alkoxy, $C_1$-$C_5$-halogenoalkoxy comprising up to 9 halogen atoms that can be the same or different or $C_1$-$C_5$-halogenoalkyl comprising up to 9 halogen atoms that can be the same or different, a heterocycle of formula ($A^{13}$)

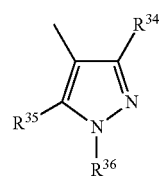

($A^{13}$)

wherein:
$R^{34}$ represents a hydrogen atom, a halogen atom, $C_1$-$C_5$-alkyl, $C_3$-$C_5$-cycloalkyl, $C_1$-$C_5$-halogenoalkyl comprising up to 9 halogen atoms that can be the same or different, $C_1$-$C_5$-alkoxy, $C_2$-$C_5$-alkynyloxy or $C_1$-$C_5$-halogenoalkoxy comprising up to 9 halogen atoms that can be the same or different, $R^{35}$ represents a hydrogen atom, a halogen atom, $C_1$-$C_5$-alkyl, a cyano, $C_1$-$C_5$-alkoxy, $C_1$-$C_5$-alkylsulphanyl, $C_1$-$C_5$-halogenoalkyl comprising up to 9 halogen atoms that can be the same or different, $C_1$-$C_5$-halogenoalkoxy comprising up to 9 halogen atoms that can be the same or different, amino, $C_1$-$C_5$-alkylamino or di($C_1$-$C_5$-alkyl)amino, $R^{36}$ represents a hydrogen atom or $C_1$-$C_5$-alkyl, a heterocycle of formula ($A^{14}$)

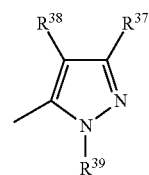

($A^{14}$)

wherein:
$R^{37}$ and $R^{38}$, independently represents a hydrogen atom, a halogen atom, $C_1$-$C_5$-alkyl, $C_1$-$C_5$-halogenoalkyl comprising up to 9 halogen atoms which can be the same or different, $C_1$-$C_5$-alkoxy, $C_1$-$C_5$-halogenoalkoxy comprising up to 9 halogen atoms that can be the same or different, or a $C_1$-$C_5$-alkylsulfanyl, $R^{39}$ represents a hydrogen atom or $C_1$-$C_5$-alkyl, a heterocycle of formula ($A^{15}$)

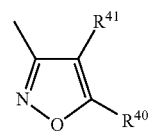

($A^{15}$)

wherein:
$R^{40}$ and $R^{41}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, a heterocycle of formula ($A^{16}$)

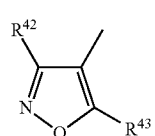

($A^{16}$)

wherein:
$R^{42}$ and $R^{43}$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different or amino, a heterocycle of formula ($A^{17}$)

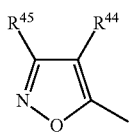

wherein:

$R^{44}$ and $R^{45}$ independently represents a hydrogen atom, a halogen atom, $C_1$-$C_5$-alkyl, $C_1$-$C_5$-halogenoalkyl comprising up to 9 halogen atoms which can be the same or different, $C_1$-$C_5$-alkoxy or $C_1$-$C_5$-halogenoalkoxy comprising up to 9 halogen atoms that can be the same or different, a heterocycle of formula ($A^{18}$)

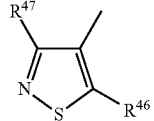

wherein:

$R^{47}$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, $R^{46}$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different or $C_1$-$C_5$-alkylsulphanyl, a heterocycle of formula ($A^{19}$)

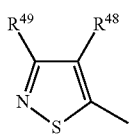

wherein:

$R^{48}$ and $R^{49}$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkyl comprising up to 9 halogen atoms that can be the same or different or $C_1$-$C_5$-alkylsulphanyl, a heterocycle of formula ($A^{20}$)

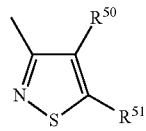

wherein:

$R^{50}$ and $R^{51}$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkyl comprising up to 9 halogen atoms that can be the same or different or $C_1$-$C_5$-alkylsulphanyl, a heterocycle of formula ($A^{21}$)

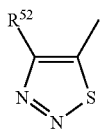

wherein:

$R^{52}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, a heterocycle of formula ($A^{22}$)

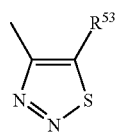

wherein:

$R^{53}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, a heterocycle of formula ($A^{23}$)

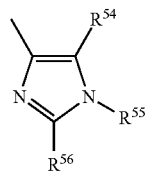

wherein:

$R^{54}$ and $R^{55}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different,
$R^{56}$ represents a hydrogen atom or $C_1$-$C_5$-alkyl,
a heterocycle of formula ($A^{24}$)

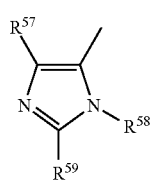

wherein:
$R^{57}$ and $R^{59}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different,
$R^{58}$ represents a hydrogen atom or $C_1$-$C_5$-alkyl,
a heterocycle of formula ($A^{25}$)

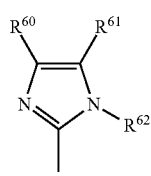

wherein:
$R^{60}$ and $R^{61}$ independently represents a hydrogen atom, a halogen atom, $C_1$-$C_5$-alkyl or $C_1$-$C_5$-halogenoalkyl comprising up to 9 halogen atoms that can be the same or different,
$R^{62}$ represents a hydrogen atom or $C_1$-$C_5$-alkyl,
a heterocycle of formula ($A^{26}$)

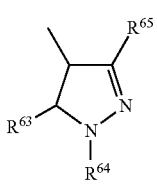

wherein:
$R^{63}$ represents a hydrogen atom, a halogen atom, $C_1$-$C_5$-alkyl, a cyano, $C_1$-$C_5$-alkoxy, $C_1$-$C_5$-alkylsulphanyl, $C_1$-$C_5$-halogenoalkyl comprising up to 9 halogen atoms that can be the same or different, $C_1$-$C_5$-halogenoalkoxy comprising up to 9 halogen atoms that can be the same or different, amino, $C_1$-$C_5$-alkylamino or di($C_1$-$C_5$-alkyl)amino,
$R^{64}$ represents a hydrogen atom or $C_1$-$C_5$-alkyl,
$R^{65}$ represents a hydrogen atom, a halogen atom, $C_1$-$C_5$-alkyl, $C_3$-$C_5$-cycloalkyl, $C_1$-$C_5$-halogenoalkyl comprising up to 9 halogen atoms that can be the same or different, $C_1$-$C_5$-alkoxy, $C_2$-$C_5$-alkynyloxy or $C_1$-$C_5$-halogenoalkoxy comprising up to 9 halogen atoms that can be the same or different.

More preferred compounds of formula (I) according to the invention are those wherein A is selected in the list consisting of $A^2$, $A^6$, $A^{10}$ and $A^{13}$.

Even more preferred compounds according to the invention are those wherein A represents $A^{13}$, wherein $R^{34}$ represents $C_1$-$C_5$-alkyl or $C_1$-$C_5$-halogenoalkyl comprising up to 9 halogen atoms that can be the same or different, $R^{35}$ represents a hydrogen or a fluorine atom, and $R^{36}$ represents methyl.

Other preferred compounds according to the invention are those wherein T represents O.

Other preferred compounds of formula (I) according to the invention are those wherein $Z^1$ represents a substituted or non-substituted cyclopropyl.

Other more preferred compounds according to the invention are those wherein $Z^1$ represents a non-substituted cyclopropyl.

Other preferred compounds of formula (I) according to the invention are those wherein $Y^1$ represents $C_1$-$C_5$-alkyl and $Y^2$ represents a hydrogen atom.

Other more preferred compounds of formula (I) according to the invention are those wherein $Y^1$ represents methyl and $Y^2$ represents a hydrogen atom.

Other preferred compounds according to the invention are those wherein $Y^1$ and $Y^2$ both represent $C_1$-$C_5$-alkyl.

Other more preferred compounds according to the invention are those wherein $Y^1$ and $Y^2$ both represent methyl.

Other preferred compounds of formula (I) according to the invention are those wherein $Z^2$ represents a hydrogen atom.

Other preferred compounds of formula (I) according to the invention are those wherein $L^1$ represents $CZ^4Z^5$.

Other preferred compounds of formula (I) according to the invention are those wherein $L^2$ represents $CZ^4Z^5$ and m represents 1 or 2.

Other preferred compounds of formula (I) according to the invention are those wherein $Z^3$ and $Z^7$, independently represents a hydrogen atom, a halogen atom, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different.

The above mentioned preferences with regard to the substituents of the compounds of formula (I) according to the invention can be combined in various manners, either individually, partially or entirely.

These combinations of preferred features thus provide sub-classes of compounds according to the invention. Examples of such sub-classes of preferred compounds according to the invention can combine:

preferred features of A with preferred features of one or more of T, $Z^1$, $Z^2$, $Y^1$, $Y^2$, $L^1$, $L^2$, m, $Z^3$ and $Z^7$;
preferred features of T with preferred features of one or more of A, $Z^1$, $Z^2$, $Y^1$, $Y^2$, $L^1$, $L^2$, m, $Z^3$ and $Z^7$;
preferred features of $Z^1$ with preferred features of one or more of A, T, $Z^2$, $Y^1$, $Y^2$, $L^1$, $L^2$, m, $Z^3$ and $Z^7$;
preferred features of $Z^2$ with preferred features of one or more of A, T, $Z^1$, $Y^1$, $Y^2$, $L^1$, $L^2$, m, $Z^3$ and $Z^7$;
preferred features of $Y^1$ with preferred features of one or more of A, T, $Z^1$, $Z^2$, $Y^2$, $L^1$, $L^2$, m, $Z^3$ and $Z^7$;
preferred features of $Y^2$ with preferred features of one or more of A, T, $Z^1$, $Z^2$, $Y^1$, $L^1$, $L^2$, m, $Z^3$ and $Z^7$;
preferred features of $L^1$ with preferred features of one or more of A, T, $Z^1$, $Y^1$, $Y^2$, $Z^2$, $L^2$, m, $Z^3$ and $Z^7$;
preferred features of $L^2$ with preferred features of one or more of A, T, $Z^1$, $Y^1$, $Y^2$, $Z^2$, $L^1$, m, $Z^3$ and $Z^7$;
preferred features of m with preferred features of one or more of A, T, $Z^1$, $Y^1$, $Y^2$, $Z^2$, $L^1$, $L^2$, $Z^3$ and $Z^7$;

preferred features of $Z^3$ with preferred features of one or more of A, T, $Z^1$, $Y^1$, $Y^2$, $Z^2$, $L^1$, $L^2$, m and $Z^7$;

preferred features of $Z^7$ with preferred features of one or more of A, T, $Z^1$, $Y^1$, $Y^2$, $Z^2$, $L^1$, $L^2$, m and $Z^3$.

In these combinations of preferred features of the substituents of the compounds according to the invention, the said preferred features can also be selected among the more preferred features of each of A, T, $Z^1$, $Z^2$, $Y^1$, $Y^2$, $L^1$, $L^2$, m, $Z^3$ and $Z^7$ so as to form most preferred subclasses of compounds according to the invention.

The present invention also relates to a process for the preparation of compounds of formula (I). Thus according to a further aspect of the present invention there is provided a process P1 for the preparation of a compound of formula (I) as herein-defined, as illustrated by the following reaction scheme:

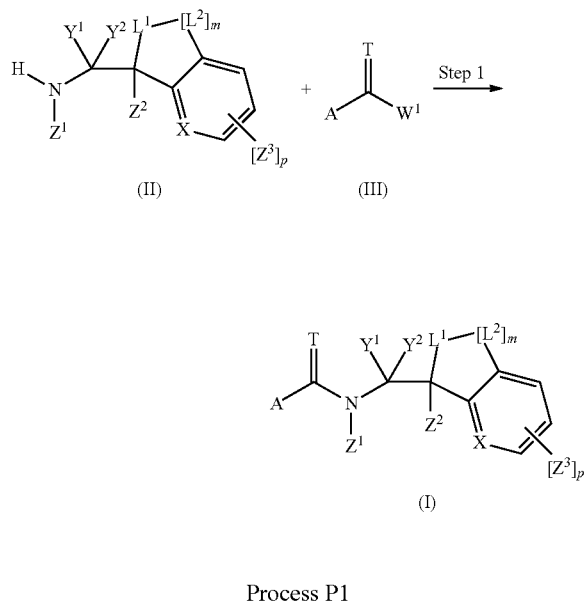

Process P1 wherein
T represents O;
$W^1$ represents a halogen atom or a hydroxyl;
A, $Z^1$ to $Z^3$, $R^a$, $R^b$, $Y^1$, $Y^2$, $L^1$, $L^2$, X, m and p are as herein-defined In process P1 according to the invention, step 1 can be performed if appropriate in the presence of a solvent and if appropriate in the presence of an acid binder.

Suitable acid binders for carrying out process P1 according to the invention can be inorganic or organic bases which are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; alkaline earth metal or alkali metal hydrides, such as sodium hydride or potassium hydride; alkaline earth metal or alkali metal alcoolates, such as sodium methylate, sodium ethylate, sodium propylate or potassium t-butylate; and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU) or a polymer-supported acid scavenger (for example as detailed in http://www.iris-biotech.de/downloads/scavengers.pdf).

It is also possible to work in the absence of any additional acid binder or to employ an excess of the amine component, so that it simultaneously acts as acid binder agent.

Suitable solvents for carrying out process P1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone, or hexamethylphosphoric triamide; alcohols such as methanol, ethanol, propanol, iso-propanol; esters, such as methyl acetate or ethyl acetate, sulphoxides, such as dimethyl sulphoxide, or sulphones, such as sulpholane.

When carrying out process P1 according to the invention, the amine derivative of formula (II) can be employed as its salt, such as chlorhydate or any other convenient salt.

When carrying out process P1 according to the invention, 1 mole or an excess of the amine derivative of formula (II) and from 1 to 3 moles of the acid binder can be employed per mole of the reagent of formula (III).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

N-cycloalkyl-amine derivatives of formula (II) can be, for example, prepared according to the following reaction scheme

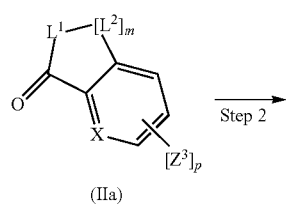

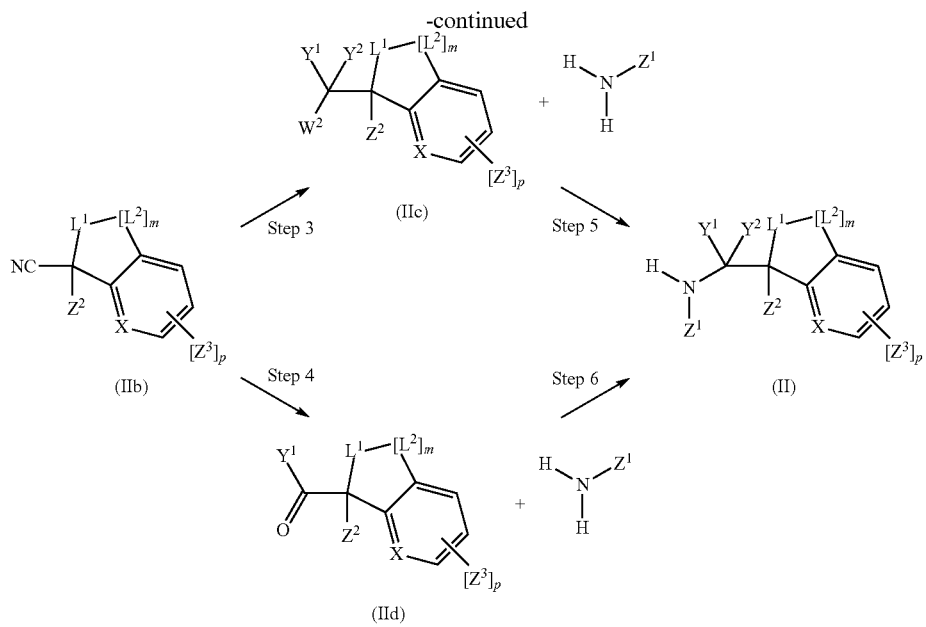

wherein
W2 represents a leaving group such as halogen atom or an hydroxy derivatives
$Z^1$ to $Z^3$, $Y^1$, $Y^2$, $L^1$, $L^2$, X, m and p are as herein-defined Derivatives of formula (IIa) are known.

When $Z^2$ represents hydroxyl or $C_1$-$C_8$ alkoxy, Step 2 is known as the Strecker reaction (Pataï, The chemistry of functional groups, SupplementC, pt. 2, 1983, p1345)
  Modified version of the Strecker synthesis may afford (IIb) when $Z^2$ represents hydrogen atom as in Synt. Comm. 1982, p763-770
  when $Z^2$ represents $C_1$-$C_8$-alkyl or $C_1$-$C_8$-halogenoalkyl comprising up to 9 halogen atoms that can be the same or different as described in J. Org. Chem., 1990, p1479-1483.
  when $Z^2$ represents amino or C1-C8-alkyl amino, as in Russ. Chem. Rev, 1989, p148

Step 3 and 4 are known conversions of cyano group to other carbonyl (IId) or alkene functions (IIc)

Step 5 is known as nucleophilic substitution and step 6 is known as reductive amination.

For preparing all compounds of formula (IIc and (IId) according to the définitions of $Z^1$ to $Z^3$, $Y^1$, $Y^2$, $L^1$, $L^2$, X, m, p and $W^2$, there are a large number of suitable known standard methods. The choice of the preparation methods which are suitables are depending on the properties of the substituents in the intermediates.

When T represents O, carboxylic acid derivatives of formula (III) are known or can be prepared by known processes (WO-93/11117, EP-A 0 545 099, Nucleosides & Nucleotides, 1987, p737-759, Bioorg. Med. Chem., 2002, p2105-2108).

Suitable acid binders for carrying out process P1 according to the invention can be inorganic or organic bases which are customary for such reactions. Preference is given to using alkaline earth metal or alkali metal hydroxides, such as sodium hydroxide, calcium hydroxide, potassium hydroxide or other ammonium hydroxide derivatives, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkaline earth metal or alkali metal hydrides, such as sodium hydride or potassium hydride, alkaline earth metal or alkali metal alcoolates, such as sodium methylate, sodium ethylate, sodium propylate or potassium t-butylate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU) or a polymer-supported acid scavenger (for example as detailed in http://www.iris-biotech.de/downloads/scavengers.pdf).

It is also possible to work in the absence of any additional acid binder or to employ an excess of the amine component, so that it simultaneously acts as acid binder agent.

Suitable solvents for carrying out process P1 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl t-butyl ether, methyl t-amyl ether, dioxane, tetrahydrofuran, 1,2-dimethoxyethane, 1,2-diethoxyethane or anisole, nitriles, such as acetonitrile, propionitrile, n- or i-butyronitrile or benzonitrile, amides, such as N,N-dimethylformamide, N,N-dimethylacetamide, N-methylformanilide, N-methylpyrrolidone, or hexamethylphosphoric triamide, alcohols such as methanol, ethanol, propanol, iso-propanol, esters, such as methyl acetate or ethyl acetate, sulphoxides, such as dimethyl sulphoxide, or sulphones, such as sulpholane.

When carrying out process P1 according to the invention, the amine derivative of formula (II) can be employed as its salt, such as chlorhydate or any other convenient salt.

When carrying out process P1 according to the invention, 1 mole or an excess of the amine derivative of formula (II) and from 1 to 3 moles of the acid binder can be employed per mole of the reagent of formula (III).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

According to a further aspect according to the invention, there is provided a process P2 for the preparation of a compound of formula (I) wherein T represents S, as herein-defined, as illustrated by the following reaction scheme:

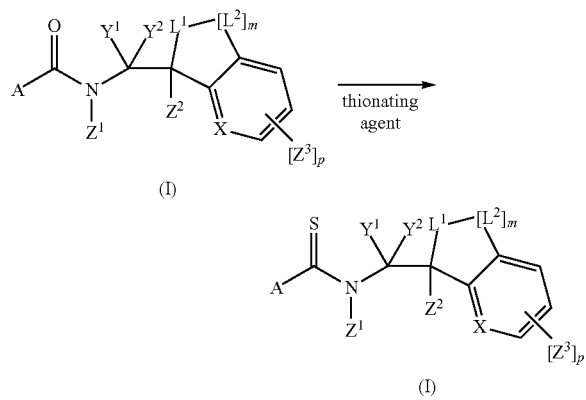

Process P2 wherein A, $Z^1$ to $Z^3$, $Y^1$, $Y^2$, $L^1$, $L^2$, X, m, p and Y are as herein-defined, Process P2 can be performed in the presence of a thionating agent.

Starting amide derivatives of formula (I) can be prepared according to process P1 wherein T represents O.

Suitable thionating agents for carrying out process P2 according to the invention can be sulphur (S), sulfhydric acid ($H_2S$), sodium sulfide ($Na_2S$), sodium hydrosulfide (NaHS), boron trisulfide ($B_2S_3$), bis (diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358. in the presence or not of a catalytic, stoechiometric or more amount of a base such as an inorganic or organic base. Preference is given to using alkali metal carbonates, such as sodium carbonate, potassium carbonate, potassium bicarbonate, sodium bicarbonate, heterocyclic aromatic bases, such as pyridine, picoline, lutidine, collidine, and also tertiary amines, such as trimethylamine, triethylamine, tributylamine, N,N-dimethylaniline, N,N-dimethylaminopyridine or N-methylpiperidine.

Suitable solvents for carrying out process P2 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl t-butyl ether, methyl t-amyl ether, dioxane, tetrahydrofuran, 1,2-dimethoxyethane or 1,2-diethoxyethane, nitriles, such as acetonitrile, propionitrile, n- or i-butyronitrile or benzonitrile, sulphurous solvents, such as sulpholane or carbon disufide.

When carrying out process P2 according to the invention, 1 mole or an excess of the sulphur equivalent of the thionating agent and from 1 to 3 moles of the base can be employed per mole of the amide reactant (I).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

When carrying out processes P1 and P2 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Processes P1 and P2 according to the invention are generally carried out under atmospheric pressure. It is also possible to operate under elevated or reduced pressure.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

Still in a further aspect, the present invention relates to compounds of formula (II) useful as intermediate compounds or materials for the process of preparation according to the invention.

The present invention thus provides compounds of formula (IIe)

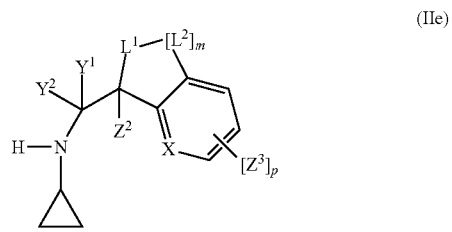

(IIe)

wherein $Z^2$, $Y^1$, $Y^2$, $L^1$, $L^2$, m, X, $Z^3$ and p are as herein-defined providing that (IIe) does not represent N-[(5-methoxy-1,2,3,4-tetrahydronaphthalen-1-yl)methyl]cyclopropanamine or 3-cyclohexyl-1-[(cyclopropylamino)methyl]-3,4-dihydro-1H-isochromene-5,6-diol.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops, and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:
(1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.
(2) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide and 5-chloro-7-(4-methylpiperidin-1-yl)-6-(2,4,6-trifluorophenyl)[1,2,4]triazolo[1,5-a]pyrimidine.
(3) inhibitors of the respiratory chain at complex I or II, for example diflumetorim as CI-respiration inhibitor;
bixafen, boscalid, carboxin, diflumetorim, fenfuram, fluopyram, flutolanil, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide and 3-(difluoromethyl)-N-[4-fluoro-2-(1,1,2,3,3,3-hexafluoropropoxy)phenyl]-1-methyl-1H-pyrazole-4-carboxamide CII-respiration inhibitor,
amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl 2-{2-[({cyclopropyl[(4-methoxyphenyl)imino]methyl}sulfanyl)methyl]phenyl}-3-methoxyacrylate and N-(3-ethyl-3,5,5-trimethylcyclohexyl)-3-(formylamino)-2-hydroxybenzamide as CIII-respiration inhibitor.
(4) Compounds capable to act as an uncoupler, like for example binapacryl, dinocap, ferimzone, fluazinam and meptyldinocap.
(5) Inhibitors of the ATP production, for example fentin acetate, fentin chloride, fentin hydroxide and silthiofam.

(6) Inhibitors of the amino acid and/or protein biosynthesis, for example andoprim, blasticidin-S, cyprodinil, kasugamycin, kasugamycin hydrochloride hydrate, mepanipyrim and pyrimethanil.

(7) Inhibitors of the signal transduction, for example chlozolinate, fenpiclonil, fludioxonil, iprodione, procymidone, quinoxyfen and vinclozolin.

(8) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]-2,2-dimethylpropyl}1H-imidazole-1-carbothioate,

(10) Inhibitors of the cell wall synthesis, for example benthiavalicarb, dimethomorph, flumorph, iprovalicarb, mandipropamid, polyoxins, polyoxorim, validamycin A and valifenalate.

(11) Inhibitors of the melanine biosynthesis, for example carpropamid, diclocymet, fenoxanil, phthalide, pyroquilon and tricyclazole,

(12) Compounds capable to induce a host defence, like for example acibenzolar-S-methyl, isotianil, probenazole and tiadinil.

(13) Compounds capable to have a multisite action, like for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(14) Further compounds like for example 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-[(4-methoxyphenoxy)methyl]-2,2-dimethylpropyl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-butoxy-6-iodo-3-propyl-4H-chromen-4-one, 2-phenylphenol and salts, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-prop-2-yn-1-ylthiophene-2-sulfonohydrazide, 5-methyl-6-octyl-3,7-dihydro[1,2,4]triazolo[1,5-a]pyrimidin-7-amine, ametoctradin, benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomate, ethyl (2Z)-3-amino-2-cyano-3-phenylprop-2-enoate, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy) imino][6-(difluoromethoxy)-2,3-difluorophenyl]methyl}-2-phenylacetamide, N-{(Z)-[(cyclopropylmethoxy) imino][6-(difluoromethoxy)-2,3-difluorophenyl]methyl}-2-phenylacetamide, natamycin, nickel dimethyldithiocarbamate, nitrothal-isopropyl, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, octhilinone, oxamocarb, oxyfenthiin, pentachlorophenol and salts, pentyl {6-[({[(1-methyl-1H-tetrazol-5-yl)(phenyl)methylidene]amino}oxy)methyl]pyridin-2-yl}carbamate, phenazine-1-carboxylic acid, phenothrin, phosphorous acid and its salts, propamocarb-fosetylate, propanosine-sodium, proquinazid, pyrrolnitrine, quinolin-8-ol, quinolin-8-ol sulfate (2:1) (salt), fenpyrazamine, tebufloquin, tecloftalam, tolnifanide, triazoxide, trichlamide and zarilamid.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can further-more be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988), 263, 4280-4289), or an *Eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084, 082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol. (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants as described in WO 2000/004173 or WO2006/045633 or PCT/EP07/004,142.

b. plants which contain a stress tolerance enhancing transgene capable of reducing the expression and/or the activity of the PARG encoding genes of the plants or plants cells, as described e.g. in WO 2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. Nos. 5,824,790, 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. Nos. 6,284,479, 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 1998/000549 b) Plants, such as cotton plants, containing an altered form of rsw2 or rsw3 homologous nucleic acids as described in WO2004/053219 c) Plants, such as cotton plants, with increased expression of sucrose phosphate synthase as described in WO 2001/017333 d) Plants, such as cotton plants, with increased expression of sucrose synthase as described in WO02/45485 e) Plants, such as cotton plants, wherein the timing of the plasmodesmatal gating at the basis of the fiber cell is altered, e.g. through downregulation of fiberselective β1,3-glucanase as described in WO 2005/017157 f) Plants, such as cotton plants, having fibers with altered reactivity, e.g. through the expression of N-acteylglucosaminetransferase gene including nodC and chitinsynthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content as described in U.S. Pat. Nos. 6,270,828, 6,169,190 or 5,965,755 c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

Among the diseases of plants or crops that can be controlled by the method according to the invention, mention can be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;

Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondite*, *Puccinia graminis* or *Puccinia striiformis*;
*Uromyces* diseases, caused for example by *Uromyces appendiculatus*;

Oomycete diseases such as:
*Albugo* diseases caused for example by *Albugo candida*;
*Bremia* diseases, caused for example by *Bremia lactucae*;
*Peronospora* diseases, caused for example by *Peronospora pisi* or *P. brassicae*;

*Phytophthora* diseases, caused for example by *Phytophthora infestans*;

*Plasmopara* diseases, caused for example by *Plasmopara viticola*;

*Pseudoperonospora* diseases, caused for example by *Pseudoperonospora humuli* or *Pseudoperonospora cubensis*;

*Pythium* diseases, caused for example by *Pythium ultimum*;

Leafspot, leaf blotch and leaf blight diseases such as:

*Alternaria* diseases, caused for example by *Alternaria solani*;

*Cercospora* diseases, caused for example by *Cercospora beticola*;

*Cladiosporum* diseases, caused for example by *Cladiosporium cucumerinum*;

*Cochliobolus* diseases, caused for example by *Cochliobolus sativus* (Conidiaform: Drechslera, Syn: *Helminthosporium*) or *Cochliobolus miyabeanus*;

*Colletotrichum* diseases, caused for example by *Colletotrichum lindemuthanium*;

*Cycloconium* diseases, caused for example by *Cycloconium oleaginum*;

*Diaporthe* diseases, caused for example by *Diaporthe citri*;

*Elsinoe* diseases, caused for example by *Elsinoe fawcettii*;

*Gloeosporium* diseases, caused for example by *Gloeosporium laeticolor*;

*Glomerella* diseases, caused for example by *Glomerella cingulata*;

*Guignardia* diseases, caused for example by *Guignardia bidwelli*;

*Leptosphaeria* diseases, caused for example by *Leptosphaeria maculans*; *Leptosphaeria nodorum*;

*Magnaporthe* diseases, caused for example by *Magnaporthe grisea*;

*Mycosphaerella* diseases, caused for example by *Mycosphaerella graminicola*; *Mycosphaerella arachidicola*; *Mycosphaerella fijiensis*;

*Phaeosphaeria* diseases, caused for example by *Phaeosphaeria nodorum*;

*Pyrenophora* diseases, caused for example by *Pyrenophora teres*, or *Pyrenophora tritici repentis*;

*Ramularia* diseases, caused for example by *Ramularia collo-cygni*, or *Ramularia areola*;

*Rhynchosporium* diseases, caused for example by *Rhynchosporium secalis*;

*Septoria* diseases, caused for example by *Septoria apii* or *Septoria lycopercisi*;

*Typhula* diseases, caused for example by *Typhula incamata*;

*Venturia* diseases, caused for example by *Venturia inaequalis*;

Root, Sheath and stem diseases such as:

*Corticium* diseases, caused for example by *Corticium graminearum*;

*Fusarium* diseases, caused for example by *Fusarium oxysporum*;

*Gaeumannomyces* diseases, caused for example by *Gaeumannomyces graminis*;

*Rhizoctonia* diseases, caused for example by *Rhizoctonia solani*;

*Sarocladium* diseases caused for example by *Sarocladium oryzae*;

*Sclerotium* diseases, caused for example by *Sclerotium oryzae*;

*Tapesia* diseases, caused for example by *Tapesia acuformis*;

*Thielaviopsis* diseases, caused for example by *Thielaviopsis basicola*;

Ear and panicle diseases such as:

*Alternaria* diseases, caused for example by *Alternaria* spp.;

*Aspergillus* diseases, caused for example by *Aspergillus flavus*;

*Cladosporium* diseases, caused for example by *Cladosporium* spp.;

*Claviceps* diseases, caused for example by *Claviceps purpurea*;

*Fusarium* diseases, caused for example by *Fusarium culmorum*;

*Gibberella* diseases, caused for example by *Gibberella zeae*;

*Monographella* diseases, caused for example by *Monographella nivalis*;

Smut and bunt diseases such as:

*Sphacelotheca* diseases, caused for example by *Sphacelotheca reiliana*;

*Tilletia* diseases, caused for example by *Tilletia caries*;

*Urocystis* diseases, caused for example by *Urocystis occulta*;

*Ustilago* diseases, caused for example by *Ustilago nuda*;

Fruit rot and mould diseases such as:

*Aspergillus* diseases, caused for example by *Aspergillus flavus*;

*Botrytis* diseases, caused for example by *Botrytis cinerea*;

*Penicillium* diseases, caused for example by *Penicillium expansum*;

*Rhizopus* diseases caused by example by *Rhizopus stolonifer*

*Sclerotinia* diseases, caused for example by *Sclerotinia sclerotiorum*;

*Verticilium* diseases, caused for example by *Verticilium alboatrum*;

Seed and soilborne decay, mould, wilt, rot and damping-off diseases:

*Alternaria* diseases, caused for example by *Alternaria brassicicola*

*Aphanomyces* diseases, caused for example by *Aphanomyces euteiches*

*Ascochyta* diseases, caused for example by *Ascochyta lentis*

*Aspergillus* diseases, caused for example by *Aspergillus flavus*

*Cladosporium* diseases, caused for example by *Cladosporium herbarum*

*Cochliobolus* diseases, caused for example by *Cochliobolus sativus* (Conidiaform: *Drechslera, Bipolaris* Syn: *Helminthosporium*);

*Colletotrichum* diseases, caused for example by *Colletotrichum coccodes*;

*Fusarium* diseases, caused for example by *Fusarium culmorum*;

*Gibberella* diseases, caused for example by *Gibberella zeae*;

*Macrophomina* diseases, caused for example by *Macrophomina phaseolina*

*Monographella* diseases, caused for example by *Monographella nivalis*;

*Penicillium* diseases, caused for example by *Penicillium expansum*

*Phoma* diseases, caused for example by *Phoma lingam*

*Phomopsis* diseases, caused for example by *Phomopsis sojae;*
*Phytophthora* diseases, caused for example by *Phytophthora cactorum;*
*Pyrenophora* diseases, caused for example by *Pyrenophora graminea*
*Pyricularia* diseases, caused for example by *Pyricularia oryzae;*
*Pythium* diseases, caused for example by *Pythium ultimum;*
*Rhizoctonia* diseases, caused for example by *Rhizoctonia solani;*
*Rhizopus* diseases, caused for example by *Rhizopus oryzae*
*Sclerotium* diseases, caused for example by *Sclerotium rolfsii;*
*Septoria* diseases, caused for example by *Septoria nodorum;*
*Typhula* diseases, caused for example by *Typhula incarnate;*
*Verticillium* diseases, caused for example by *Verticillium dahliae;*
Canker, broom and dieback diseases such as:
*Nectria* diseases, caused for example by *Nectria geffigena;*
Blight diseases such as:
*Monilinia* diseases, caused for example by *Monilinia lexa;*
Leaf blister or leaf curl diseases such as:
*Exobasidium* diseases caused for example by *Exobasidium vexans*
*Taphrina* diseases, caused for example by *Taphrina deformans;*
Decline diseases of wooden plants such as:
*Esca* diseases, caused for example by *Phaemoniella clamydospora;*
*Eutypa* dyeback, caused for example by *Eutypa late;*
*Ganoderma* diseases caused for example by *Ganoderma boninense;*
*Rigidoporus* diseases caused for example by *Rigidoporus lignosus*
Diseases of Flowers and Seeds such as
*Botrytis* diseases caused for example by *Botrytis cinerea;*
Diseases of Tubers such as
*Rhizoctonia* diseases caused for example by *Rhizoctonia solani;*
*Helminthosporium* diseases caused for example by *Helminthosporium solani;*
Club root diseases such as
*Plasmodiophora* diseases, cause for example by *Plamodiophora brassicae.*
Diseases caused by Bacterial Organisms such as
*Xanthomonas* species for example *Xanthomonas campestris* pv. *oryzae;*
*Pseudomonas* species for example *Pseudomonas syringae* pv. *lachrymans;*
*Erwinia* species for example *Erwinia amylovora.*

The fungicide composition according to the invention can also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention, this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The various aspects of the invention will now be illustrated with reference to the following table of active or intermediate compound examples and the following preparation or efficacy examples.

The following tables illustrate in a non-limiting manner examples of active or intermediate compounds according to the invention.

In the following table, M+H (or M−H) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

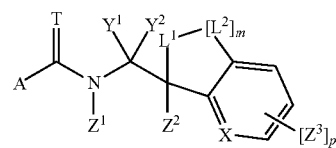

| Example | | $Y^1$ | $Y^2$ | $Z^1$ | T | A | M + H | logP |
|---|---|---|---|---|---|---|---|---|
| I.1 | HO-tetrahydronaphthalene | Me | H | cPr | O | fluoropyrazole | 372 | 2.78 |

-continued

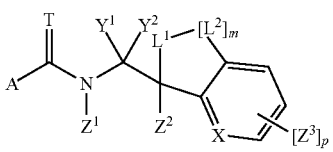

| Example | [structure] | Y¹ | Y² | Z¹ | T | A | M + H | logP |
|---|---|---|---|---|---|---|---|---|
| I.2 | [tetrahydronaphthalenyl] | Me | H | cPr | O | [methyl-fluoro-pyrazolyl] | 356 | 3.55 |
| I.3 | [tetrahydronaphthalenyl] | Me | H | cPr | S | [methyl-fluoro-pyrazolyl] | 372 | 4.39 |
| I.4 | [8-Br-tetrahydronaphthalenyl] | Me | H | cPr | O | [methyl-fluoro-pyrazolyl] | | |
| I.5 | [2,2-dimethylchromanyl] | H | H | cPr | O | [methyl-fluoro-pyrazolyl] | 372 | 3.04 |
| I.6 | [1-HO-tetrahydronaphthalenyl] | Me | H | cPr | S | [ethyl-fluoro-pyrazolyl] | 386 | 3.23 |
| I.7 | [tetrahydronaphthalenyl] | Me | H | cPr | O | [ethyl-fluoro-pyrazolyl] | | |
| I.8 | [2,2-dimethylchromanyl] | H | H | cPr | O | [ethyl-fluoro-pyrazolyl] | 366 | 3.39 |
| I.9 | [8-Br-tetrahydronaphthalenyl] | Me | H | cPr | O | [ethyl-fluoro-pyrazolyl] | | |

-continued
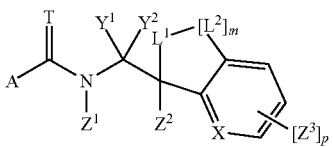
| Example | | Y¹ | Y² | Z¹ | T | A | M + H | logP |
|---|---|---|---|---|---|---|---|---|
| 1.10 | 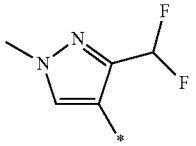 | Me | H | cPr | O | 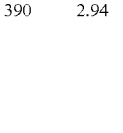 | 390 | 2.94 |
| 1.11 | 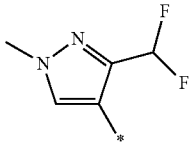 | Me | H | cPr | O |  | | |
| I.12 | 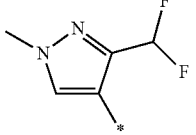 | Me | H | cPr | O |  | | |
| I.13 | 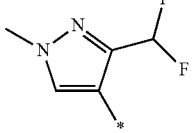 | H | H | cPr | O |  | 390 | 3.17 |
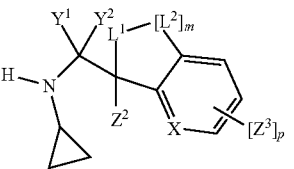
| Example | | Y¹ | Y² | M + H | logP | Example | | Y¹ | Y² | M + H | logP |
|---|---|---|---|---|---|---|---|---|---|---|---|
| IIe.1 | 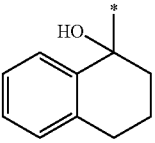 [SMILES: *C1(O)CCCc2ccccc21] | Me | H | 232 | | IIe.2 | 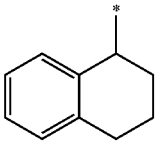 [SMILES: *C1CCCc2ccccc21] | Me | H | | |

-continued

| Example | structure | Y¹ | Y² | M + H | logP |
|---|---|---|---|---|---|
| IIe.3 | (8-bromo-tetrahydronaphthalenyl) | Br | * Me | H | |
| IIe.4 | (2,2-dimethylchroman-4-yl) | * | H | H | 232 |

The following examples illustrate in a non-limiting manner the preparation and efficacy of the compounds of formula (I) according to the invention.

PREPARATION EXAMPLE

N-cyclopropyl-3-(difluoromethyl)-N-[1-(1-hydroxy-1,2,3,4-tetrahydro naphthalen-1-yl)ethyl]-1-methyl-1H-pyrazole-4-carboxamide (compound I.10)

Step 1: preparation of 1-[1-(cyclopropylamino) ethyl]-1,2,3,4-tetrahydronaphthalen-1-ol (compound IIe.1)

To a solution of 3.97 ml (57.3 mmol) of cyclopropylamine and 3.3 ml (57.3 mmol) of acetic acid, together with 3 Å molecular sieves, in 30 ml of methanol, are added 5.45 g (28.7 mmol) of 1-(1-hydroxy-1,2,3,4-tetrahydronaphthalen-1-yl) ethanone. The reaction mixture is stirred for 5 hrs at reflux. The reaction mixture is then cooled to ambient temperature and 2.70 g (43.0 mmol) of sodium cyanoborohydride are slowly added. The reaction mixture is further stirred for 2 hrs at reflux and at RT overnight. The reaction mixture is filtered over celite and washed with methanol. The solvent is removed under vacuum and the residue is dissolved in ethyl acetate and the solution is washed twice with 1N aqeuous NaOH and then once with water; the organic layer is dried over magnesium sulphate and concentrated in vacuum to yield a yellow oil which contains a majority of 1-[1-(cyclopropylamino)ethyl]-1,2,3,4-tetrahydronaphthalen-1-ol (M+1=232)

Step 2: preparation of N-cyclopropyl-3-(difluoromethyl)-N-[1-(1-hydroxy-1,2,3,4-tetrahydronaphthalen-1-yl)ethyl]-1-methyl-1H-pyrazole-4-carboxamide At ambient temperature, a solution of 0.198 g (1.02 mmol) of 5-fluoro-1,3-dimethyl-1H-pyrazole-4-carbonyl chloride, 0.215 g (0.93 mmol) of 1-[1-(cyclopropylamino)ethyl]-1,2,3,4-tetrahydronaphthalen-1-ol and 0.26 ml triethylamine in 5 ml tetrahydrofurane is stirred overnight. The solvent is removed under vacuum and 10 ml of water are then added to the residue The watery layer is extracted twice with ethyl acetate; the combined organic layers are dried over magnesium sulphate and concentrated in vacuum. Column chromatography (gradient n-heptane/ethyl acetate) yields 0.138 mg (38% yield) of N-cyclopropyl-3-(difluoromethyl)-N-[1-(1-hydroxy-1,2,3,4-tetrahydronaphthalen-1-yl)ethyl]-1-methyl-1H-pyrazole-4-carboxamide (M+1=390).

PREPARATION EXAMPLE

N-cyclopropyl-5-fluoro-1,3-dimethyl-N-[1-(1,2,3,4-tetrahydronaphthalen-1-yl)ethyl]-1H-pyrazole-4-carbothioamide (compound I.3)

A solution of 70 mg (0.19 mmol) of N-cyclopropyl-5-fluoro-1,3-dimethyl-N-[1-(1,2,3,4-tetrahydronaphthalen-1-yl)ethyl]-1H-pyrazole-4-carboxamide (obtained as in first preparation example) and 22 mg (0.08 mmol) of phosphorous pentasulfide in 10 ml of dry dioxane is heated at 100° C. for 1 h 30. After cooling, 2 ml of water is added and the solution is extracted with ethyl acetate. The combined organic layers are washed with an saturated Na2CO3 aqueous solution, then with brine, dried over magnesium sulphate and concentrated in vacuum. Column chromatography (gradient n-heptane/ethyl acetate) yields 40 mg of the expected product.

EFFICACY EXAMPLE A

*Alternaria* Test (Tomato)/Preventive

Solvent: 49 parts by weight of N,N-Dimethylformamide
Emulsifier: 1 part by weight of Alkylarylpolyglycolether
To produce a suitable preparation of active compound, 1 part by weight of active compound is mixed with the stated amounts of solvent and emulsifier, and the concentrate is diluted with water to the desired concentration.
To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%.
The test is evaluated 7 days after the inoculation. 0% means an efficacy which corresponds to that of the control while an efficacy of 100% means that no disease is observed.
In this test the compounds according to the invention of the following structures showed efficacy of 70% or even higher at a concentration of 500 ppm of active ingredient: 1.1, 1.2, 1.8, 1.10 and 1.13,

EFFICACY EXAMPLE B

*Pyrenophora* Test (Barley)/Preventive

Solvent: 49 parts by weight of N,N-Dimethylformamide
Emulsifier: 1 part by weight of Alkylarylpolyglycolether
To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the control while an efficacy of 100% means that no disease is observed.

In this test the compounds according to the invention of the following structures showed efficacy of 70% or even higher at a concentration of 500 ppm of active ingredient: 1.1, 1.2, 1.8, 1.10 and 1.13,

EFFICACY EXAMPLE C

*Leptosphaeria Nodorum* Test (Wheat)/Preventive

Solvent: 49 parts by weight of n,n-dimethylacetamid
Emulsifier: 1 part by weight of alkylaryl polyglycol ether To produce a suitable preparation of active compound, 1 part by weight of active compound or the compound combination is mixed with the stated amounts of solvent and emulsifier, and the concentrate is diluted with water to the desired concentration.

To test for protective activity, young plants are sprayed with a preparation of active compound or active compound combination at the stated rate of application. After the spray coating has dried on, the plants are sprayed with a spore suspension of *Leptosphaeria nodorum*. The plants remain for 48 hours in an incubation cabinet at 20° C. and a relative atmospheric humidity of 100%.

The plants are placed in a greenhouse at a temperature of approximately 15° C. and a relative atmospheric humidity of approximately 80%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 500 ppm of active ingredient: 1.1, 1.8 and 1.13.

EFFICACY EXAMPLE D

*Septoria Tritici*-Test (Wheat)/Preventive

Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application. After the spray coating has dried on, the plants are sprayed with a spore suspension of *Septoria tritici*. The plants remain for 48 hours in an incubation cabinet at approximately 20° C. and a relative atmospheric humidity of approximately 100% and then 60 hours at approximately 15° C. in a translucent incubation cabinet at a relative atmospheric humidity of approximately 100%.

The plants are placed in a greenhouse at a temperature of approximately 15° C. and a relative atmospheric humidity of approximately 80%.

The test is evaluated 21 days after the inoculation. 0% means an efficacy which corresponds to that of the control, while an efficacy of 100% means that no disease is observed.

In this test the following compounds according to the invention showed an efficacy of 70% or even higher at a concentration of 500 ppm of active ingredient 1.1, 1.8 and 1.13.

EXAMPLE E

Efficacy Against *Puccinia* Triticina

Solvent: 49 parts by weight of n,n-dimethylacetamid
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a spore suspension of *Puccinia* triticina. The plants remain for 48 hours in an incubation cabinet at approximately 20° C. and a relative atmospheric humidity of approximately 100%.

2 days later the plants are sprayed with the preparation of active compound or active compound combination at the stated rate of application.

The plants are placed in a greenhouse at a temperature of approximately 20° C. and a relative atmospheric humidity of approximately 80%.

The test is evaluated 8 days after the inoculation. 0% means an efficacy which corresponds to that of the control, while an efficacy of 100% means that no disease is observed.

In this test the following compounds according to the invention showed an efficacy of 60% or even higher at a concentration of 500 ppm of active ingredient 1.1, 1.6 and 1.8 whereas no protection is observed at a dose of 500 ppm with the compounds F-3 and F-5 disclosed in international patent WO2007060164.

The invention claimed is:
1. A compound of formula (I)

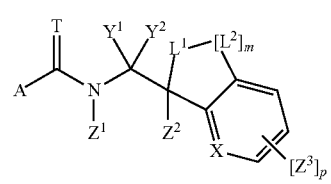

wherein
A represents a carbo-linked, partially saturated or unsaturated, 5-membered heterocyclyl group that can be substituted by up to four groups R that can be the same or different,
T represents O or S,
$Z^1$ represents a non substituted $C_3$-$C_7$-cycloalkyl or a $C_3$-$C_7$ cycloalkyl substituted by up to 10 atoms or groups that can be the same or different and that can be selected in the list consisting of halogen atoms, cyano, $C_1$-$C_8$-alkyl,$C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, di-$C_1$-$C_8$-alkylaminocarbonyl or carbamoyl, $Z^2$ represents a hydrogen atom, a halogen atom, hydroxyl group, cyano, $C_1$-$C_8$-alkyl, $C_1$-$C_8$-alkoxy, $C_1$-$C_8$-halogenoalkyl comprising up to 9 halogen atoms that can be the same or different, amino or $C_1$-$C_8$-alkylamino $Y^1$ and $Y^2$ independently represents an hydrogen atom, an halogen atom, cyano, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, di-$C_1$-$C_8$-alkylaminocarbonyl or carbamoyl, $L^1$ and $L^2$ independently represents $CZ^4Z^5$, $NZ^6$, O, S, S(O) or $S(O)_2$, m represents 1, 2 or 3, X represents $CZ^7$ or N, $Z^3$ and $Z^7$ independently represents a hydrogen atom, a halogen atom, nitro, cyano, hydroxyl, thio, amino, pentafluoro-λ6-thio, $C_1$-$C_8$-alkyl, $C_1$-$C_8$-halogenoalkyl comprising up to 9 halogen atoms that can be the same or different, $C_1$-$C_8$-arylalkyl, $(C_3$-$C_7$-cycloalkyl)-$C_1$-$C_8$alkyl, $C_1$-$C_8$-alkylamino, di-$C_1$-$C_8$-alkylamino, $C_1$-$C_8$alkoxy, $C_1$-$C_8$-halogenoalkoxy comprising up to 9 halogen atoms that can be the same or different, $C_1$-$C_8$-alkoxy-$C_1$-$C_8$-alkyl, $C_1$-$C_8$-alkylsulphanyl, $C_1$-$C_8$-halogenoalkylsulphanyl comprising up to 9 halogen atoms that can be the same or different, $C_2$-$C_8$-alkenyl, $C_2$-$C_8$-halogenoalkenyl comprising up to 9 halogen atoms that can be the same or different, $C_1$-$C_8$-arylalkenyl, $(C_3$-$C_7$-cycloalkyl)-$C_1$-$C_8$alkenyl, $C_2$-$C_8$-alkynyl, $C_2$-$C_8$-halogenoalkynyl comprising up to 9 halogen atoms that can be the same or different, $C_1$-$C_8$-arylalkynyl, $(C_3$-$C_7$-cycloalkyl)-$C_1$-$C_8$-alkynyl, $C_2$-$C_8$-alkenyloxy, $C_2$-$C_8$-halogenoalkenyloxy comprising up to 9 halogen atoms that can be the same or different, $C_2$-$C_8$-alkynyloxy, $C_2$-$C_8$-halogenoalkynyloxy comprising up to 9 halogen atoms that can be the same or different, $C_3$-$C_7$-cycloalkyl, $C_3$-$C_7$-cycloalkyl-$C_1$-$C_8$alkyl, $C_3$-$C_7$-halogenocycloalkyl comprising up to 9 halogen atoms that can be the same or different, formyl, formyloxy, formylamino, carboxy, carbamoyl, N-hydroxycarbamoyl, carbamate, (hydroxyimino)-$C_1$-$C_8$-alkyl, $C_1$-$C_8$-alkylcarbonyl, $C_1$-$C_8$-halogenoalkylcarbonyl comprising up to 9 halogen atoms that can be the same or different, $C_1$-$C_8$-alkylcarbamoyl, di-$C_1$-$C_8$-alkylcarbamoyl, N—$C_1$-$C_8$-alkyloxycarbamoyl, $C_1$-$C_8$-alkoxycarbamoyl, N—$C_1$-$C_8$-alkyl-$C_1$-$C_8$-alkoxycarbamoyl, $C_1$-$C_8$-alkoxycarbonyl, $C_1$-$C_8$-halogenoalkoxycarbonyl comprising up to 9 halogen atoms that can be the same or different, $C_1$-$C_8$-alkylaminocarbonyl, di-$C_1$-$C_8$alkylaminocarbonyl, $C_1$-$C_8$alkylcarbonyloxy, $C_1$-$C_8$-halogenoalkylcarbonyloxy comprising up to 9 halogen atoms that can be the same or different, $C_1$-$C_8$-alkylcarbonylamino, $C_1$-$C_8$-halogenoalkylcarbonylamino comprising up to 9 halogen atoms that can be the same or different, $C_1$-$C_8$-alkylaminocarbonyloxy, di-$C_1$-$C_8$-alkylaminocarbonyloxy, $C_1$-$C_8$-alkyloxycarbonyloxy, $C_1$-$C_8$-alkylsulphenyl, $C_1$-$C_8$-halogenoalkylsulphenyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, $C_1$-$C_8$-halogeno-alkylsulphonyl comprising up to 9 halogen atoms that can be the same or different, $C_1$-$C_8$-alkoxyimino, $(C_1$-$C_8$-alkoxyimino)-$C_1$-$C_8$-alkyl, $(C_1$-$C_8$-alkenyloxyimino)-$C_1$-$C_8$-alkyl, $(C_1$-$C_8$-alkynyloxyimino)-$C_1$-$C_8$-alkyl, a (benzyloxyimino)-$C_1$-$C_8$-alkyl, tri($C_1$-$C_8$-alkyl)silyl, tri($C_1$-$C_8$-alkyl)silyl-$C_1$-$C_8$-alkyl, phenyl that can be substituted by up to 5 groups Q that can be the same or different, benzyloxy that can be substituted by up to 5 groups Q that can be the same or different, benzylthio that can be substituted by up to 5 groups Q that can be the same or different, benzylamino that can be substituted by up to 5 groups Q that can be the same or different, naphtyl that can be substituted by up to 6 groups Q that can be the same or different, phenoxy that can be substituted by up to 5 groups Q that can be the same or different, phenylamino that can be substituted by up to 5 groups Q that can be the same or different, phenylthio that can be substituted by up to 5 groups Q that can be the same or different, phenylmethylene that can be substituted by up to 5 groups Q that can be the same or different, pyridinyl that can be substituted by up to four groups Q that can be the same or different, pyridinyloxy that can be substituted by up to four groups Q that can be the same or different, or phenoxymethylene that can be substituted by up to 5 groups Q; or $Z^3$ or $Z^7$ together with the consecutive carbon atoms to which they are linked can form a 5- or 6-membered, saturated or non-saturated, carbo- or hetero-cycle, that can be substituted by up to four groups Q that can be the same or different, p represents 1, 2, or 3, R represents hydrogen atom, halogen atom, cyano, nitro, amino, thio, pentafluoro-λ-6-thio, $C_1$-$C_8$-alkylamino, di-$C_1$-$C_8$-alkylamino, tri($C_1$-$C_8$-alkyl)silyl, $C_1$-$C_8$-alkylsulphanyl, $C_1$-$C_8$-halogenoalkylsulphanyl comprising up to 9 halogen atoms that can be the same or different, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_1$-$C_8$-alkoxy, $C_1$-$C_8$-halogenoalkoxy comprising up to 9 halogen atoms that can be the same or different, $C_2$-$C_8$-alkenyloxy, $C_2$-$C_8$-alkynyloxy, $C_3$-$C_7$-cycloalkyl, $C_3$-$C_7$-cycloalkyl-$C_1$-$C_8$-alkyl, $C_1$-$C_8$-alkylsulphinyl, $C_1$-$C_8$-alkylsulphonyl, $C_1$-$C_8$alkoxyimino, $(C_1$-$C_8$-alkoxyimino)-$C_1$-$C_8$-alkyl, (benzyloxyimino)-$C_1$-$C_8$-alkyl, phenoxy, benzyloxy, benzylthio, benzylamino, naphtyl, halogenophenoxy comprising up to 9 halogen atoms that can be the same or different, $C_1$-$C_8$-alkylcarbonyl, $C_1$-$C_8$-halogenoalkylcarbonyl comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$alkylaminocarbonyl, or di-$C_1$-$C_8$alkylaminocarbonyl, $Z^4$ and $Z^5$ independently represents a hydrogen atom, a halogen atoms, cyano, nitro, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkoxy-$C_1$-$C_8$-alkyl, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms that can be the same or different, formyl, $C_1$-$C_8$-alkylcarbonyl, $C_1$-$C_8$-halogenoalkylcarbonyl comprising up to 9 halogen atoms that can be the same or different, $C_1$-$C_8$-alkylsulphanyl, $C_1$-$C_8$-halogenoalkylsulphanyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, or $C_1$-$C_8$-halogenoalkylsulphonyl comprising up to 9 halogen atoms that can be the same or different, $Z^6$ represents a hydrogen atom, $C_1$-$C_8$-alkyl, $C_1$-$C_8$-halogenoalkyl comprising up to 9 halogen atoms that can be the same or different, $C_1$-$C_8$-alkoxy-$C_1$-$C_8$-alkyl, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms that can be the same or different, formyl, $C_1$-$C_8$-alkylcarbonyl, $C_1$-$C_8$-halogenoalkylcarbonyl comprising up to 9 halogen atoms that can be the same or different, $C_1$-$C_8$-alkylsulphonyl, $C_1$-$C_8$-halogenoalkylsulphonyl comprising up to 9 halogen atoms that can be the same or different, phenylsulfonyl can be substituted by up to 5 groups Q that can be the same or different, or benzyl that can be substituted by up to 5 groups Q that can be the same or different, Q represents a halogen atom, cyano, nitro, $C_1$-$C_8$-alkyl, $C_1$-$C_8$-halogenoalkyl comprising up to 9 halogen atoms that can be the same or different, $C_1$-$C_8$-alkoxy, $C_1$-$C_8$-halogenoalkoxy comprising up to 9 halogen atoms that can be the same or different, $C_1$-$C_8$-alkylsulphanyl, $C_1$-$C_8$-halogenoalkylsulphanyl comprising up to 9 halogen atoms that can be the same or different, tri($C_1$-$C_8$)alkylsilyl or tri($C_1$-$C_8$)alkylsilyl-$C_1$-$C_8$-alkyl, as well as salts, N-oxides, and optically active or geometric isomers thereof.

2. A compound according to claim 1 wherein A is selected in the list consisting of:

a heterocycle of formula ($A^1$)

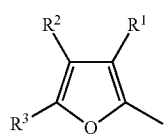

wherein:
$R^1$ to $R^3$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy or $C_1$-$C_5$-halogenoalkoxy comprising up to 9 halogen atoms that can be the same or different, a heterocycle of formula ($A^2$)

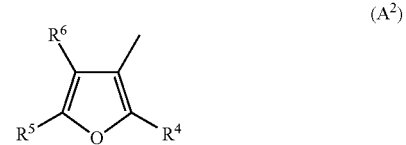

wherein:
$R^4$ to $R^6$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy or $C_1$-$C_5$-halogenoalkoxy comprising up to 9 halogen atoms that can be the same or different, a heterocycle of formula ($A^3$)

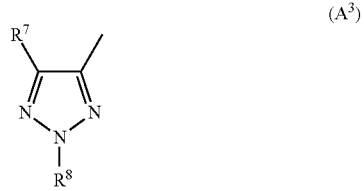

wherein:
$R^7$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy or $C_1$-$C_5$-halogenoalkoxy comprising up to 9 halogen atoms that can be the same or different;
$R^8$ represents a hydrogen atom or a $C_1$-$C_5$-alkyl, a heterocycle of formula ($A^4$)

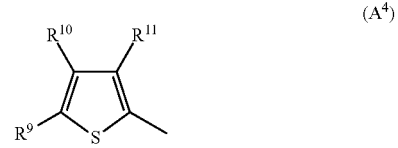

wherein:
$R^9$, $R^{10}$, $R^{11}$ independently represents a hydrogen atom, a halogen atom, $C_1$-$C_5$-alkyl, amino, $C_1$-$C_5$-alkoxy, $C_1$-$C_5$-alkylsulphanyl, $C_1$-$C_5$-halogenoalkyl comprising up to 9 halogen atoms that can be the same or different or $C_1$-$C_5$-halogenoalkoxy comprising up to 9 halogen atoms that can be the same or different, a heterocycle of formula ($A^5$)

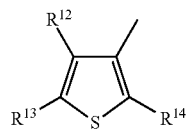

wherein:
$R^{12}, R^{13}, R^{14}$ independently represents a hydrogen atom, a halogen atom, $C_1$-$C_5$-alkyl, $C_1$-$C_5$-alkoxy, amino, $C_1$-$C_5$-halogenoalkyl comprising up to 9 halogen atoms that can be the same or different or $C_1$-$C_5$-halogenoalkoxy comprising up to 9 halogen atoms that can be the same or different, a heterocycle of formula $(A^6)$

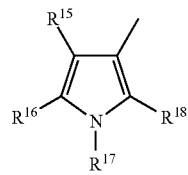

wherein:
$R^{15}$ represents a hydrogen atom, a halogen atom, a cyano, $C_1$-$C_5$-alkyl, $C_1$-$C_5$-alkoxy, $C_1$-$C_5$-halogenoalkoxy comprising up to 9 halogen atoms that can be the same or different or $C_1$-$C_5$-halogenoalkyl comprising up to 9 halogen atoms that can be the same or different, $R^{16}$ and $R^{18}$ independently represents a hydrogen atom, a halogen atom, $C_1$-$C_5$-alkoxycarbonyl, $C_1$-$C_5$-alkyl, $C_1$-$C_5$-halogenoalkoxy comprising up to 9 halogen atoms that can be the same or different or $C_1$-$C_5$-halogenoalkyl comprising up to 9 halogen atoms that can be the same or different, $R^{17}$ represents a hydrogen atom or $C_1$-$C_5$-alkyl, a heterocycle of formula $(A^7)$

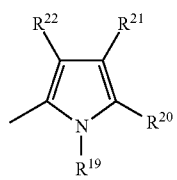

wherein:
$R^{19}$ represents a hydrogen atom or a $C_1$-$C_5$-alkyl,
$R^{20}, R^{21}, R^{22}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, a heterocycle of formula $(A^8)$

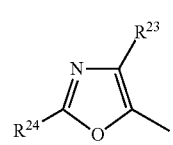

wherein:
$R^{23}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, $R^{24}$ represents a hydrogen atom or $C_1$-$C_5$-alkyl or $C_1$-$C_5$-halogenoalkyl comprising up to 9 halogen atoms that can be the same or different, a heterocycle of formula $(A^9)$

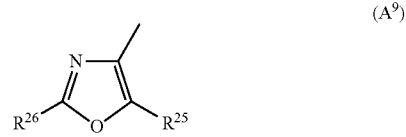

wherein:
$R^{25}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, $R^{26}$ represents a hydrogen atom, $C_1$-$C_5$-alkyl or $C_1$-$C_5$-halogenoalkyl comprising up to 9 halogen atoms that can be the same or different, a heterocycle of formula $(A^{10})$

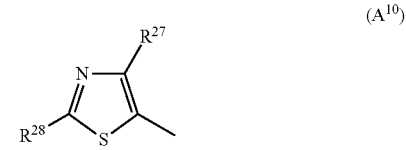

wherein:
$R^{27}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, $R^{28}$ represents a hydrogen atom, a halogen atom, amino, $C_1$-$C_5$-alkyl or $C_1$-$C_5$-halogenoalkyl comprising up to 9 halogen atoms that can be the same or different, $C_1$-$C_5$-alkoxy, C1-C5-halogenoalkoxy comprising up to 9 halogen atoms which can be the same or different, $C_1$-$C_5$-alkylsulfanyl or $C_1$-$C_5$-halogenoalkylsulfanyl comprising up to 9 halogen atoms that can be the same or different, $C_1$-$C_5$-alkylamino or di($C_1$-$C_5$-alkyl)amino, a heterocycle of formula $(A^{11})$

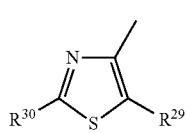

wherein:
$R^{29}$ represents a hydrogen atom, a halogen atom, $C_1$-$C_5$-alkyl, $C_1$-$C_5$-alkoxy, $C_1$-$C_5$-halogenoalkoxy comprising up to 9 halogen atoms that can be the same or different or $C_1$-$C_5$-halogenoalkyl comprising up to 9 halogen atoms that can be the same or different, $R^{30}$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, $C_1$-$C_5$-alkylsulfanyl or $C_1$-$C_5$-halogenoalkylsulfanyl comprising up to 9 halogen atoms that can be the same or different, amino, $C_1$-$C_5$-alkylamino or di-$C_1$-$C_5$-alkylamino, a heterocycle of formula ($A^{12}$)

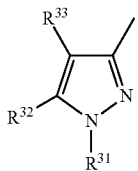

wherein:
$R^{31}$ represents a hydrogen atom, a halogen atom or a $C_1$-$C_5$-alkyl,
$R^{32}$ represents a hydrogen atom, a halogen atom, $C_1$-$C_5$-alkyl or $C_1$-$C_5$-halogenoalkyl comprising up to 9 halogen atoms that can be the same or different,
$R^{33}$ represents a hydrogen atom, a halogen atom, a nitro, $C_1$-$C_5$-alkyl, $C_1$-$C_5$-alkoxy, $C_1$-$C_5$-halogenoalkoxy comprising up to 9 halogen atoms that can be the same or different or $C_1$-$C_5$-halogenoalkyl comprising up to 9 halogen atoms that can be the same or different, a heterocycle of formula ($A^{13}$)

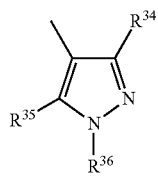

wherein:
$R^{34}$ represents a hydrogen atom, a halogen atom, $C_1$-$C_5$-alkyl, $C_3$-$C_5$-cycloalkyl, $C_1$-$C_5$-halogenoalkyl comprising up to 9 halogen atoms that can be the same or different, $C_1$-$C_5$-alkoxy, $C_2$-$C_5$-alkynyloxy or $C_1$-$C_5$-halogenoalkoxy comprising up to 9 halogen atoms that can be the same or different,
$R^{35}$ represents a hydrogen atom, a halogen atom, $C_1$-$C_5$-alkyl, a cyano, $C_1$-$C_5$-alkoxy, $C_1$-$C_5$-alkylsulphanyl, $C_1$-$C_5$-halogenoalkyl comprising up to 9 halogen atoms that can be the same or different, $C_1$-$C_5$-halogenoalkoxy comprising up to 9 halogen atoms that can be the same or different, amino, $C_1$-$C_5$-alkylamino or di($C_1$-$C_5$-alkyl)amino,
$R^{36}$ represents a hydrogen atom or $C_1$-$C_5$-alkyl,
a heterocycle of formula ($A^{14}$)

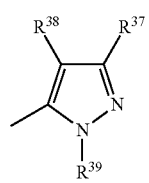

wherein:
$R^{37}$, and $R^{38}$ independently represents a hydrogen atom, a halogen atom, $C_1$-$C_5$-alkyl, $C_1$-$C_5$-halogenoalkyl comprising up to 9 halogen atoms which can be the same or different, $C_1$-$C_5$-alkoxy, $C_1$-$C_5$-halogenoalkoxy comprising up to 9 halogen atoms that can be the same or different, or a $C_1$-$C_5$-alkylsulfanyl,
$R^{39}$ represents a hydrogen atom or $C_1$-$C_5$-alkyl,
a heterocycle of formula ($A^{15}$)

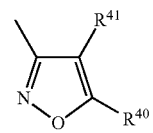

wherein:
$R^{40}$ and $R^{41}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, a heterocycle of formula ($A^{16}$)

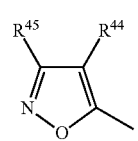

wherein:
$R^{42}$ and $R^{43}$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different or amino, a heterocycle of formula ($A^{17}$)

wherein:
$R^{44}$ and $R^{45}$ independently represents a hydrogen atom, a halogen atom, $C_1$-$C_5$-alkyl, $C_1$-$C_5$-halogenoalkyl comprising up to 9 halogen atoms which can be the same or different, $C_1$-$C_5$-alkoxy or $C_1$-$C_5$-halogenoalkoxy comprising up to 9 halogen atoms that can be the same or different, a heterocycle of formula ($A^{18}$)

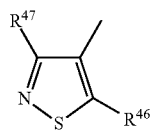

($A^{18}$)

wherein:

$R^{47}$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different, $R^{46}$ represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different or $C_1$-$C_5$-alkylsulphanyl, a heterocycle of formula ($A^{19}$)

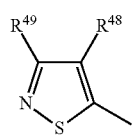

($A^{19}$)

wherein:

$R^{48}$ and $R^{49}$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkyl comprising up to 9 halogen atoms that can be the same or different or $C_1$-$C_5$-alkylsulphanyl, a heterocycle of formula ($A^{20}$)

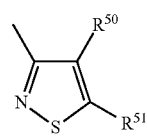

($A^{20}$)

wherein:

$R^5$ and $R^{51}$ independently represents a hydrogen atom, a halogen atom, $C_1$-$C_5$-alkyl, $C_1$-$C_5$-halogenoalkyl comprising up to 9 halogen atoms that can be the same or different, $C_1$-$C_5$-alkoxy, $C_1$-$C_5$-halogenoalkyl comprising up to 9 halogen atoms that can be the same or different or $C_1$-$C_5$-alkylsulphanyl, a heterocycle of formula ($A^{21}$)

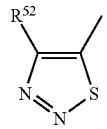

($A^{21}$)

wherein:

$R^{52}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, a heterocycle of formula ($A^{22}$)

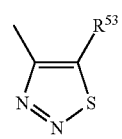

($A^{22}$)

wherein:

$R^{53}$ represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, a heterocycle of formula ($A^{23}$)

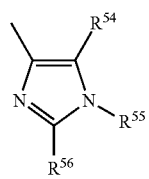

($A^{23}$)

wherein:

$R^{54}$ and $R^{55}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, $C_1$-$C_5$-halogenoalkoxy comprising up to 9 halogen atoms that can be the same or different, $R^{56}$ represents a hydrogen atom or $C_1$-$C_5$-alkyl, a heterocycle of formula ($A^{24}$)

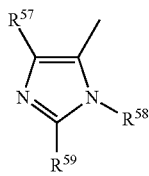

($A^{24}$)

wherein:
- $R^{57}$ and $R^{59}$ independently represents a hydrogen atom, a halogen atom, $C_1$-$C_5$-alkyl or $C_1$-$C_5$-halogenoalkyl comprising up to 9 halogen atoms that can be the same or different, $C_1$-$C_5$-alkoxy, or $C_1$-$C_5$-halogenoalkoxy comprising up to 9 halogen atoms that can be the same or different,
- $R^{58}$ represents a hydrogen atom or $C_1$-$C_5$-alkyl, a heterocycle of formula ($A^{25}$)

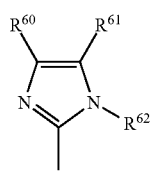

wherein:
- $R^{60}$ and $R^{61}$ independently represents a hydrogen atom, a halogen atom, $C_1$-$C_5$-alkyl or $C_1$-$C_5$-halogenoalkyl comprising up to 9 halogen atoms that can be the same or different,
- $R^{62}$ represents a hydrogen atom or $C_1$-$C_5$-alkyl, a heterocycle of formula ($A^{26}$)

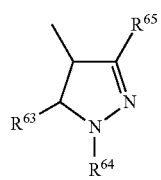

wherein:
- $R^{63}$ represents a hydrogen atom, a halogen atom, $C_1$-$C_5$-alkyl, a cyano, $C_1$-$C_5$-alkoxy, $C_1$-$C_5$-alkylsulphanyl, $C_1$-$C_5$-halogenoalkyl comprising up to 9 halogen atoms that can be the same or different, $C_1$-$C_5$-halogenoalkoxy comprising up to 9 halogen atoms that can be the same or different, amino, $C_1$-$C_5$-alkylamino or di($C_1$-$C_5$-alkyl)amino,
- $R^{64}$ represents a hydrogen atom or $C_1$-$C_5$-alkyl,
- $R^{65}$ represents a hydrogen atom, a halogen atom, $C_1$-$C_5$-alkyl, $C_3$-$C_5$-cycloalkyl, $C_1$-$C_5$-halogenoalkyl comprising up to 9 halogen atoms that can be the same or different, $C_1$-$C_5$-alkoxy, $C_2$-$C_5$-alkynyloxy or $C_1$-$C_5$-halogenoalkoxy comprising up to 9 halogen atoms that can be the same or different.

3. A compound according to claim 2 wherein A is selected in the list consisting of $A^2$, $A^6$, $A^{10}$ and $A^{13}$.

4. A compound according to claim 3 wherein A represents $A^{13}$, wherein $R^{34}$ represents $C_1$-$C_5$-alkyl or $C_1$-$C_5$-halogenoalkyl comprising up to 9 halogen atoms that can be the same or different, $R^{35}$ represents a hydrogen or a fluorine atom and $R^{36}$ represents methyl.

5. A compound according to claim 1 wherein T represents O.

6. A compound according to claim 1 wherein $Z^1$ represents a substituted or non-substituted cyclopropyl.

7. A compound according to claim 6 wherein $Z^1$ represents a non-substituted cyclopropyl.

8. A compound according to claim 1 wherein $Y^1$ represents $C_1$-$C_5$-alkyl and $Y^2$ represents hydrogen.

9. A compound according to claim 8 wherein wherein $Y^1$ represents methyl and $Y^2$ represents hydrogen.

10. A compound according to claim 1 wherein $Y^1$ and $Y^2$ both represent $C_1$-$C_5$-alkyl.

11. A compound according to claim 10 wherein $Y^1$ and $Y^2$ both represent methyl.

12. A compound according to claim 1 wherein $Z^2$ represents a hydrogen atom.

13. A compound according to claim 1 wherein $L^1$ represents $CZ^4Z^5$.

14. A compound according to claim 1 wherein $L^2$ represents $CZ^4Z^5$ and m represents 1 or 2.

15. A compound according to claim 1 wherein $Z^3$ and $Z^7$ independently represents a hydrogen atom, a halogen atom, $C_1$-$C_8$-alkyl, $C_1$-$C_8$-halogenoalkyl comprising up to 9 halogen atoms that can be the same or different, $C_1$-$C_8$-alkoxy or $C_1$-$C_8$-halogenoalkoxy comprising up to 9 halogen atoms that can be the same or different.

16. A fungicide composition comprising, as an active ingredient, an effective amount of a compound of formula (I) according to claim 1 and an agriculturally acceptable support, carrier or filler.

17. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

18. A method for controlling phytopathogenic fungi of crops, characterized in that an agronomically effective and substantially non-phytotoxic quantity of a composition according to claim 16 is applied to the soil where plants grow or are capable of growing, to the leaves and/or the fruit of plants or to the seeds of plants.

* * * * *